(12) United States Patent
Spier

(10) Patent No.: US 7,588,896 B2
(45) Date of Patent: *Sep. 15, 2009

(54) METHODS, COMPOSITIONS, AND KITS FOR FORMING SELF-COMPLEMENTARY POLYNUCLEOTIDES

(75) Inventor: Eugene G. Spier, Palo Alto, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 11/622,991

(22) Filed: Jan. 12, 2007

(65) Prior Publication Data

US 2007/0141610 A1 Jun. 21, 2007

Related U.S. Application Data

(63) Continuation of application No. 11/305,699, filed on Dec. 16, 2005, now Pat. No. 7,169,561.

(60) Provisional application No. 60/639,994, filed on Dec. 29, 2004.

(51) Int. Cl.
C12Q 1/68 (2006.01)
C12P 19/34 (2006.01)
C07H 21/00 (2006.01)
C07H 21/02 (2006.01)
C07H 21/04 (2006.01)

(52) U.S. Cl. .................. 435/6; 435/91.2; 536/22.1; 536/23.1; 536/24.3

(58) Field of Classification Search .............. 435/6, 435/91.2; 536/22.1, 23.1, 24.3
See application file for complete search history.

(56) References Cited

U.S. PATENT DOCUMENTS

| 5,215,899 | A | 6/1993 | Dattagupta |
| 5,470,724 | A | 11/1995 | Ahern |
| 5,494,810 | A | 2/1996 | Barany et al. |
| 5,876,924 | A | 3/1999 | Zhang et al. |
| 6,027,889 | A | 2/2000 | Barany et al. |
| 6,114,121 | A | 9/2000 | Fujiwara et al. |
| 6,498,023 | B1 | 12/2002 | Abarzua |
| 7,033,753 | B1 | 4/2006 | Kool |
| 7,169,561 | B2 * | 1/2007 | Spier .................. 435/6 |
| 7,306,915 | B2 * | 12/2007 | Daito et al. ............ 435/6 |
| 2003/0175788 | A1 | 9/2003 | Alsmadi et al. |
| 2004/0259116 | A1 | 12/2004 | Beckman et al. |
| 2005/0142559 | A1 * | 6/2005 | Makrigiorgos ........ 435/6 |
| 2008/0021205 | A1 * | 1/2008 | Blau et al. .......... 536/23.1 |

FOREIGN PATENT DOCUMENTS

| JP | 2005-304489 | * 11/2005 |
| JP | 2005-304490 | * 11/2005 |
| WO | WO 99/49079 | 9/1999 |

OTHER PUBLICATIONS

Translation of JP 2004-086958 (i.e. JP 2005-304490).*
International Search Report and Written Opinion issued in International Application No. PCT/US05/45709, mailing date Aug. 28, 2006, 9 pages.

* cited by examiner

*Primary Examiner*—Ethan Whisenant
(74) *Attorney, Agent, or Firm*—Andrew K. Finn

(57) ABSTRACT

The present teachings generally relate to methods, kits, and compositions for detecting target polynucleotide sequences. The teachings also relate to ligation and amplification reactions that generate self-complementary polynucleotide products. In some embodiments, ligation reactions are performed with probes that result in the formation a self-complementary ligation product. Ligation of a hairpin linker to the self-complementary ligation product can form a loop ligation product. In some embodiments, the loop ligation product can be amplified with rolling circle amplification. Detection of a loop ligation product can serve to determine the identity of a target polynucleotide.

16 Claims, 11 Drawing Sheets

METHODS, COMPOSITIONS, AND KITS FOR FORMING SELF-COMPLEMENTARY POLYNUCLEOTIDES

CROSS-REFERENCE TO RELATED APPLICATIONS

This application is a continuation of U.S. application Ser. No. 11/305,699, filed Dec. 16, 2005 now U.S. Pat. No. 7,169,561, which claims a priority benefit under 35 U.S.C. 119(e) from U.S. patent application Ser. No. 60/639,994, filed Dec. 29, 2004, the contents of each is incorporated herein by reference.

FIELD

The present teachings generally relate to methods, kits, and compositions for detecting target polynucleotide sequences. The teachings also relate to ligation and amplification reactions that generate self-complementary polynucleotide products.

INTRODUCTION

An increasing range of scientific disciplines involve the identification of target polynucleotide sequences. Hybridization, ligation, and amplification are procedures employed to query samples containing such target polynucleotides. The increasing amount of nucleic acid sequence information available to scientists in the post-genomics era has produced an opportunity for rapid, reliable, low-cost, high-throughput, sensitive, and accurate methods for studying target polynucleotides. The present teachings address this and other opportunities.

SUMMARY

In some embodiments, the present teachings provide a method of determining a target polynucleotide comprising; providing a target polynucleotide, and a probe set, wherein the probe set comprises a first probe, a second probe, and a hairpin linker, wherein the first probe comprises a target specific portion, a single-stranded stem portion, and a protruding tail, wherein the second probe comprises a target specific portion, and a single-stranded stem portion, wherein the hairpin linker comprises a loop portion, a stem portion, and a protruding tail,
  wherein the single-stranded stem portion of the first probe is complementary to the single-stranded stem portion of the second probe, wherein the protruding tail of the hairpin linker is complementary to the protruding tail of the first probe;
  hybridizing the first probe one and the second probe to the target polynucleotide; ligating the first probe to the second probe to form a first ligation product; dissociating the first ligation product from the target polynucleotide; hybridizing the single-stranded stem portion of the first probe to the single-stranded stem portion of the second probe to form a self-complementary ligation product; hybridizing the protruding tail of the self-complementary ligation product to the protruding tail of the hairpin linker; ligating the self-complementary ligation product to the hairpin linker to form a loop ligation product; detecting the loop ligation product; and, determining the target polynucleotide.

DESCRIPTION OF EXEMPLARY EMBODIMENTS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

SOME DEFINITIONS

As used herein, the term "probe set" refers to a collection of oligonucleotides that can query a particular target polynucleotide sequence. Typically, a probe set will comprise at least one first probe, a second probe, and a hairpin linker. In some embodiments when two first probes are present the two first probes shall be referred to as a first probe one and a first probe two, as can be the case for example in the context of detecting two allelic variants at a single nucleotide polymorphism locus.

Figure 3:
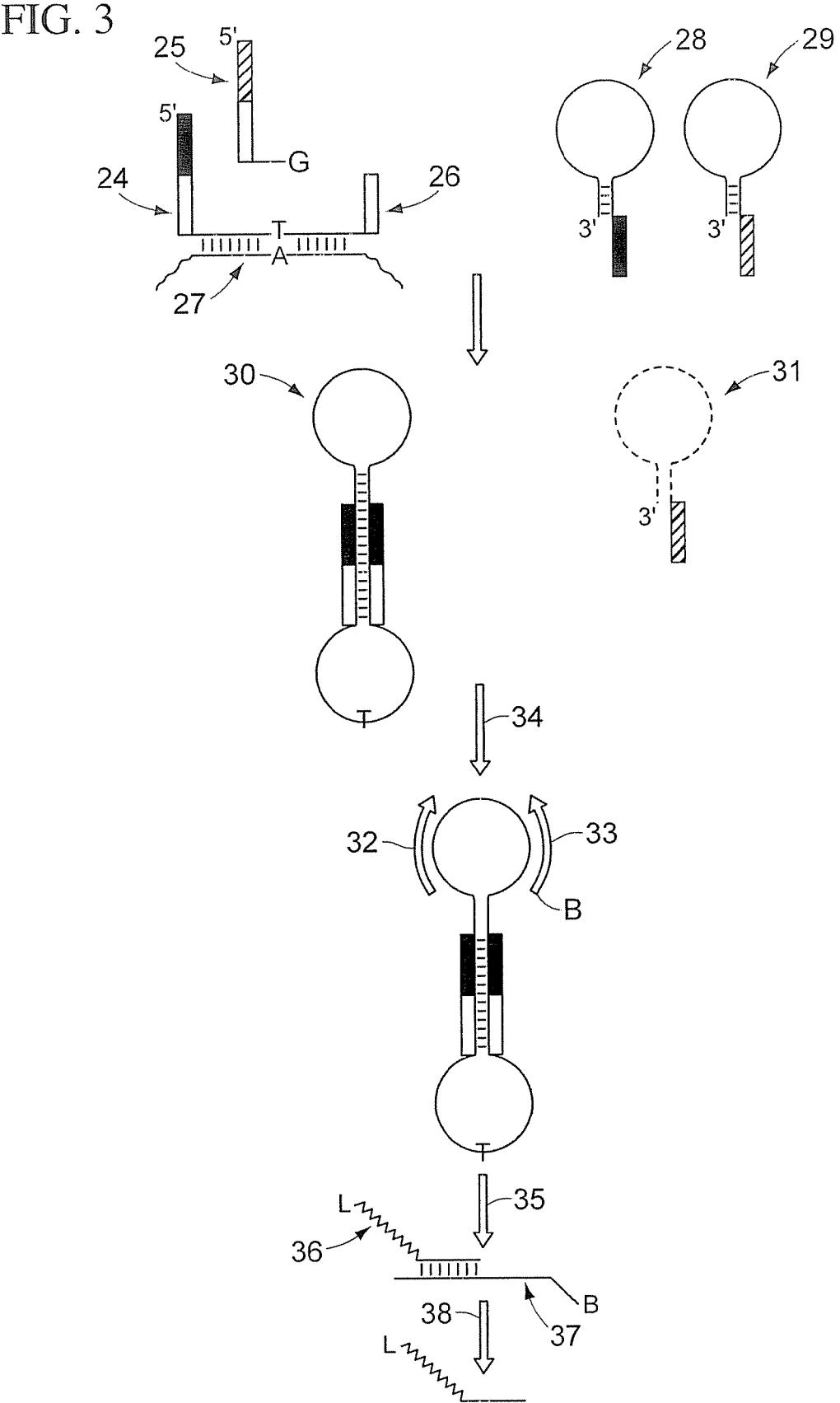
FIG. 3 illustrates a schematic embodiment contemplated by the present teachings.

As used herein, the term "first probe" refers generally to at least one oligonucleotide that can hybridize to a target polynucleotide sequence adjacent to a second probe, and that generally comprises a target specific portion, a discriminating region, a single stranded stem portion, and a protruding tail. When querying at least two allelic variants present at a particular SNP locus for example, a probe set can comprise a "first probe one" and a "first probe two," and potentially more first probes, wherein each of the first probes in a particular probe set differ in their discriminating regions and in their protruding tails, but can have the same target specific portion and the same single stranded stem portion. A non-limiting illustrative encoding scheme for a SNP locus with two possible allelic variants is shown in FIG. 3. Here, the first probes comprise a discriminating region at their 3' terminals to allow for allelic discrimination, and the first probes further have a 5' protruding tail. It will be appreciated that the present teachings further contemplate embodiments in which the discriminating nucleotide is located at the 5' end of a probe, such that for example two second probes differ in their discriminating region at their 5' end. In such an embodiment, the protruding tails can be 3' protruding tails. An example of a 3' protruding tail can be found in FIG. 5. It will be appreciated that generally the terms first probe and second probe are intended to orient the reader for the context of a given embodiment, but are not intended to be limiting.

As used herein, the term "second probe" refers generally to at least one oligonucleotide that can hybridize to a target polynucleotide sequence adjacent to at least one first probe, and that generally comprises a target specific portion and a single-stranded stem portion.

As used herein, the term "hairpin linker" refers to an oligonucleotide comprising a protruding tail that is single stranded, a double stranded stem, and a single-stranded loop. In a particular probe set, the protruding tail of the hairpin linker can be complementary to the protruding tail of a first probe, and their hybridization can allow for their ligation and the formation of a loop ligation product.

As used herein, a "target" or "target polynucleotide" according to the present teachings comprises a specific nucleic acid sequence that can be distinguished by a probe. Targets may include both naturally occurring and synthetic molecules.

As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, O6-methylguanine, N6-methyladenine, O4-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352;, and WO 99/14226). Exemplary LNA sugar analogs within a polynucleotide include, but are not limited to, the structures:

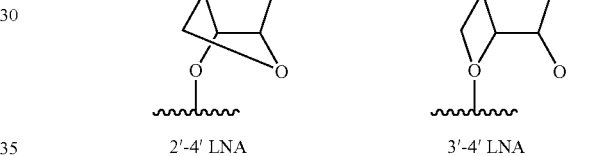

2'-4' LNA       3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the N9-position of the nucleotide base. When the nucleotide base is pyrimidine, e.g. C, T or U, the pentose sugar is attached to the N1-position of the nucleotide base, except for pseudouridines, in which the pentose sugar is attached to the C5 position of the uracil nucleotide base (see, e.g., Kornberg and Baker, (1992) DNA Replication, 2nd Ed., Freeman, San Francisco, Calif.).

One or more of the pentose carbons of a nucleotide may be substituted with a phosphate ester having the formula:

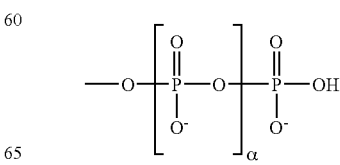

where a is an integer from 0 to 4. In certain embodiments, a is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. -thio-nucleotide 5'-triphosphates. For a review of nucleotide chemistry, see: Shabarova, Z. and Bogdanov, A. *Advanced Organic Chemistry of Nucleic Acids*, VCH, New York, 1994.

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone. Also included are intercalating nucleic acids (INAs, as described in Christensen and Pedersen, 2002), and AEGIS bases (Eragen, U.S. Pat. No. 5,432,272).

As used herein, the terms "polynucleotide", "oligonucleotide", and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H+, NH4+, trialkylammonium, Mg2+, Na+ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occuring nucleotides and nucleotide analogs. Nucleic acids typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids include, but are not limited to, genomic DNA, cDNA, hnRNA, mRNA, rRNA, tRNA, micro RNA, various non-coding RNA (ncRNAs), fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

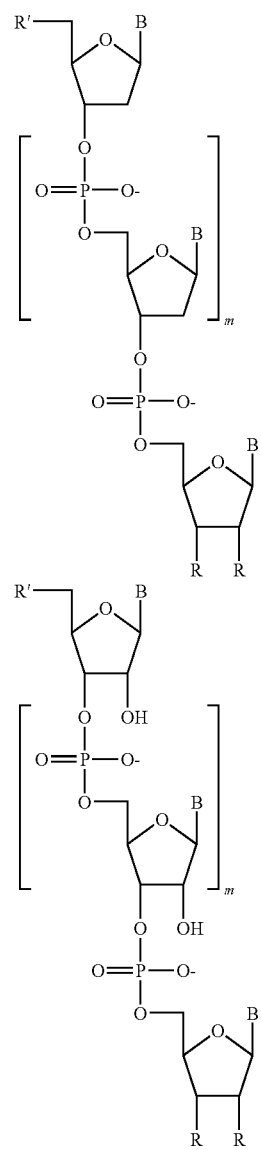

wherein each B is independently the base moiety of a nucleotide, e.g., a purine, a 7-deazapurine, a pyrimidine, or an analog nucleotide; each m defines the length of the respective nucleic acid and can range from zero to thousands, tens of thousands, or even more; each R is independently selected from the group comprising hydrogen, halogen —R", —OR", and —NR"R", where each R" is independently (C1-C6) alkyl or (C5-C14) aryl, two adjacent Rs are taken together to form a bond such that the ribose sugar is 2',3'-didehydroribose; and each R' is independently hydroxyl or

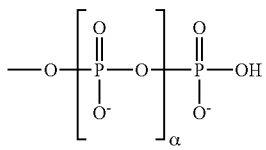

where a is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. Nos. 5,719,262; 5,698,685;); morpholinos (see, e.g., U.S. Pat. Nos. 5,698,685; 5,378,841; 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) C1C4 alkylphosphonate, e.g. methylphosphonate; (ii) phosphoramidate; (iii) C1C6 alkyl-phosphotriester; (iv) phosphorothioate; and (v) phosphorodithioate.

As used herein, the term "target specific portion" refers to the portion of a probe substantially complementary to a target polynucleotide sequence.

As used herein, the term "discriminating region" refers to a portion of a probe that can distinguish between alternate versions of a target polynucleotide. For example, when a SNP locus is queried, a first probe one can comprise a first discriminating region and a first probe two can comprise a second discriminating region, wherein the first discriminating region and the second discriminating region distinguish between a first allele and a second allele at the SNP locus. The discriminating region can be located at the 3' end of the target specific portion, or elsewhere in the target specific portion. The discriminating region as depicted herein typically comprises a single nucleotide, though it will be appreciated that additional nucleotides can be present.

As used herein, the term "single-stranded stem portion" refers to a region of a first probe and a region of a second probe that can hybridize together to form a stem.

As used herein, the term "protruding tail" refers to single stranded region that is present in the hairpin linker and first probe of a given probe set, which can hybridize together if a corresponding self-complementary ligation product is formed to result in the formation of a loop ligation product.

As used herein, the term "first ligation product" refers to a first probe that is ligated to a second probe, wherein the single stranded stem portions of the first probe and the second probe are not hybridized together.

As used herein, the term "self-complementary ligation product" refers to a first probe that is ligated to a second probe, wherein the single-stranded stem portions of the first probe and the second probe are hybridized together. Typically, a self-complementary ligation product results from the dissociation of the first ligation product from the target polynucleotide.

As used herein, the term "loop ligation product" refers to a product resulting from the hybridization and ligation of a self-complementary ligation product with a hairpin linker.

As used herein, the term "partial loop ligation product" refers to a product resulting from the hybridization and ligation of a self-complementary ligation product with a non-hairpin linker.

As used herein, the term "non-hairpin linker" refers to a double stranded molecule that further comprises a protruding tail, and comprises moieties that can confer various functional properties, including resistance to nucleases. Non-hairpin linkers can be hybridized and ligated to self-complementary ligation products to form partial loop ligation products.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "corresponding" as used herein refers to at least one specific relationship between the elements to which the term refers. For example, at least one first probe of a probe set corresponds to at least one second probe of the same probe set, and vice versa. The target-specific portions of the probes of a particular probe set can be designed to hybridize with a complementary region of the corresponding target polynucleotide sequence. A particular affinity moiety can bind to the corresponding affinity moiety binder, for example but not limited to, the affinity moiety binder streptavidin binding to the affinity moiety biotin. A particular mobility probe can hybridize with the corresponding identifier portion or target-identifying portion complement. A particular discriminating region can hybridize to the corresponding nucleotide or nucleotides on the target polynucleotide (for example the nucleotide conferring a particular allelic identity to a SNP locus). A protruding tail that is present in the hairpin linker can hybridize with the corresponding protruding tail that is present in the first probe incorporated into a corresponding self-complementary ligation product, to result in the formation of a corresponding loop ligation product.

As used herein the terms "annealing" and "hybridization" are used interchangeably and mean the complementary base-pairing interaction of one nucleic acid with another nucleic acid that results in formation of a duplex, triplex, or other higher-ordered structure. In some embodiments, the primary interaction is base specific, e.g., A/T and G/C, by Watson/Crick and Hoogsteen-type hydrogen bonding. In some embodiments, base-stacking and hydrophobic interactions may also contribute to duplex stability. Conditions for hybridizing nucleic acid probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the probes and the complementary target sequences, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. Further, in general probes and primers of the present teachings are designed to be complementary to a target sequence, such that hybridization of the target and the probes or primers occurs. It will be appreciated, however, that this complementarity need not be perfect; there can be any number of base pair mismatches that will interfere with hybridization between the target sequence and the single stranded nucleic acids of the present teachings. However, if the number of base pair mismatches is so great that no hybridization can occur under even the least stringent of hybridization conditions, the sequence is not a complementary target sequence. Thus, by "substantially complementary" herein is meant that the probes or primers are sufficiently complementary to the target sequence to hybridize under the selected reaction conditions.

As used herein, the terms "label" refers to detectable moieties that can be attached to an oligonucleotide, mobility probe, or otherwise be used in a reporter system, to thereby render the molecule detectable by an instrument or method. For example, a label can be any moiety that: (i) provides a detectable signal; (ii) interacts with a second label to modify the detectable signal provided by the first or second label; or (iii) confers a capture function, e.g. hydrophobic affinity, antibody/antigen, ionic complexation. The skilled artisan will appreciate that many different species of reporter labels can be used in the present teachings, either individually or in combination with one or more different labels. Exemplary labels include, but are not limited to, fluorophores, radioisotopes, Quantum Dots, chromogens, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, NE), electrochemiluminescence labels, including but not limited to, tris(bipyridal) ruthenium (II), also known as Ru(bpy)$_3^{2+}$, Os(1,10-phenanthroline)$_2$bis (diphenylphosphino)ethane$^{2+}$, also known as Os(phen)$_2$(dppene)$^{2+}$, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy$_3^{2+}$), and the like.

Detailed descriptions of ECL and electrochemiluminescent moieties can be found in, among other places, A. Bard and L. Faulkner, Electrochemical Methods, John Wiley & Sons (2001); M. Collinson and M. Wightman, Anal. Chem. 65:2576 et seq. (1993); D. Brunce and M. Richter, Anal. Chem. 74:3157 et seq. (2002); A. Knight, Trends in Anal. Chem. 18:47 et seq. (1999); B. Muegge et al., Anal. Chem. 75:1102 et seq. (2003); H. Abrunda et al., J. Amer. Chem. Soc. 104:2641 et seq. (1982); K. Maness et al., J. Amer. Chem. Soc. 118:10609 et seq. (1996); M. Collinson and R. Wightman.

As used herein, the term "target-identifying portion" refers to moiety or moieties that can be used to identify a particular target polynucleotide, and can refer to a variety of distinguishable moieties, including for example zipcodes and a known number of nucleobases. In some embodiments, target-identifying portion refers to an oligonucleotide sequence that can be used for separating the element to which it is bound, including without limitation, bulk separation; for tethering or attaching the element to which it is bound to a substrate, which may or may not include separating; for annealing an target-identifying portion complement that may comprise at least one moiety, such as a mobility modifier, one or more labels, and combinations thereof. The term "target-identifying portion complement" typically refers to at least one oligonucleotide that comprises at least one sequence of nucleobases that are at least substantially complementary to and hybridize with their corresponding target-identifying portion.

Typically, target-identifying portions and their corresponding target-identifying portion complements are selected to minimize: internal, self-hybridization; cross-hybridization with different target-identifying portion species, nucleotide sequences in a reaction composition, including but not limited to gDNA, different species of target-identifying portion complements, or target-specific portions of probes, and the like; but should be amenable to facile hybridization between the target-identifying portion and its corresponding target-identifying portion complement. Target-identifying portion sequences and target-identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of target-identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

In some embodiments, target-identifying portions are at least 6 bases in length, at least 8 bases in length, at least 10 bases in length, at least 12 bases in length, at least 15 bases in length, 12-60 bases in length, or 15-30 bases in length. In some embodiments, at least one target-identifying portion is 12, 15, 20, 21, 22, 23, 24, 25, 26, 27, 28, 29, 30, 45, or 60 bases in length. In some embodiments, at least two target-identifying portion: target-identifying portion complement duplexes have melting temperatures that fall within a $\Delta T_m$ range ($T_{max}$-$T_{min}$) of no more than 10° C. of each other. In some embodiments, at least two target-identifying portion: target-identifying portion complement duplexes have melting temperatures that fall within a $\Delta T_m$ range of 5° C. or less of each other. In some embodiments, at least two target-identifying portion: target-identifying portion complement duplexes have melting temperatures that fall within a $\Delta T_m$ range of 2° C. or less of each other.

In some embodiments, at least one target-identifying portion complement is annealed to at least one corresponding target-identifying portion and, subsequently, at least part of that target-identifying portion complement is released and detected.

The term "mobility modifier" as used herein refers to at least one molecular entity, for example but not limited to, at least one polymer chain, that when added to at least one element (e.g., a mobility probe) affects the mobility of the element to which it is hybridized or bound, covalently or non-covalently, in at least one mobility-dependent analytical technique. Typically, a mobility modifier changes the charge/translational frictional drag when hybridized or bound to the element; or imparts a distinctive mobility, for example but not limited to, a distinctive elution characteristic in a chromatographic separation medium or a distinctive electrophoretic mobility in a sieving matrix or non-sieving matrix, when hybridized or bound to the corresponding element; or both (see, e.g., U.S. Pat. Nos. 5,470,705 and 5,514,543). For various examples of mobility modifiers see for example U.S. Pat. Nos. 6,395,486, 6,358,385, 6,355,709, 5,916,426, 5,807,682, 5,777,096, 5,703,222, 5,556,7292, 5,567,292, 5,552,028, 5,470,705, and Barbier et al., Current Opinion in Biotechnology, 2003, 14:1:51-57

In some embodiments, at least one mobility modifier comprises at least one nucleotide polymer chain, including without limitation, at least one oligonucleotide polymer chain, at least one polynucleotide polymer chain, or both at least one oligonucleotide polymer chain and at least one polynucleotide polymer chain (see for example Published P.C.T. application WO9615271A1, as well as product literature for Keygene SNPWave™ for some examples of using known numbers of nucleotides to confer mobility to ligation products). In some embodiments, at least one mobility modifier comprises at least one non-nucleotide polymer chain. Exemplary non-nucleotide polymer chains include, without limitation, peptides, polypeptides, polyethylene oxide (PEO), or the like. In some embodiments, at least one polymer chain comprises at least one substantially uncharged, water-soluble chain, such as a chain composed of PEO units; a polypeptide chain; or combinations thereof.

The polymer chain can comprise a homopolymer, a random copolymer, a block copolymer, or combinations thereof. Furthermore, the polymer chain can have a linear architecture, a comb architecture, a branched architecture, a dendritic architecture (e.g., polymers containing polyamidoamine branched polymers, Polysciences, Inc. Warrington, Pa.), or combinations thereof. In some embodiments, at least one polymer chain is hydrophilic, or at least sufficiently hydrophilic when hybridized or bound to an element to ensure that the element-mobility modifier is readily soluble in aqueous medium. Where the mobility-dependent analysis technique is electrophoresis, in some embodiments, the polymer chains are uncharged or have a charge/subunit density that is substantially less than that of its corresponding element.

The synthesis of polymer chains useful as mobility modifiers will depend, at least in part, on the nature of the polymer. Methods for preparing suitable polymers generally follow well-known polymer subunit synthesis methods. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, polypeptides, oligosaccharides, and nucleotide polymers. Such methods of polymer unit coupling are also suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods (e.g., Int. J. Peptide Protein Res., 35: 161-214 (1990)).

One method for preparing PEO polymer chains having a selected number of hexaethylene oxide (HEO) units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (e.g., U.S. Pat. No. 4,914,210; see also, U.S. Pat. No. 5,777,096).

As used herein, a "mobility probe" generally refers to a molecule comprising a mobility modifier, a label, and a target-identifying portion or target-identifying portion complement that can hybridize to a ligation product or ligation product surrogate, the detection of which allows for the identification of the target polynucleotide.

As used herein, the term "mobility-dependent analytical technique" as used herein refers to any means for separating different molecular species based on differential rates of migration of those different molecular species in one or more separation techniques. Exemplary mobility-dependent analysis techniques include gel electrophoresis, capillary electrophoresis, chromatography, capillary electrochromatography, mass spectroscopy, sedimentation, e.g., gradient centrifugation, field-flow fractionation, multi-stage extraction techniques and the like. Descriptions of mobility-dependent analytical techniques can be found in, among other places, U.S. Pat. Nos. 5,470,705, 5,514,543, 5,580,732, 5,624,800, and 5,807,682, PCT Publication No. WO 01/92579, Fu et al., Current Opinion in Biotechnology, 2003, 14:1:96-100, D. R. Baker, Capillary Electrophoresis, Wiley-Interscience (1995), Biochromatography: Theory and Practice, M. A. Vijayalakshmi, ed., Taylor & Francis, London, U.K. (2003); and A. Pingoud et al., Biochemical Methods: A Concise Guide for Students and Researchers, Wiley-VCH Verlag GmbH, Weinheim, Germany (2002).

As used herein, the term "ligation agent" can comprise any number of enzymatic or non-enzymatic reagents. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids. Temperature sensitive ligases, include, but are not limited to, bacteriophage T4 ligase and *E. coli* ligase. Thermostable ligases include, but are not limited to, Afu ligase, Taq ligase, Tfl ligase, Tth ligase, Tth HB8 ligase, *Thermus* species AK16D ligase and Pfu ligase (see for example Published P.C.T. Application WO00/26381, Wu et al., Gene, 76(2):245-254, (1989), Luo et al., Nucleic Acids Research, 24(15): 3071-3078 (1996). The skilled artisan will appreciate that any number of thermostable ligases, including DNA ligases and RNA ligases, can be obtained from thermophilic or hyperthermophilic organisms, for example, certain species of eubacteria and archaea; and that such ligases can be employed in the disclosed methods and kits. Further, reversibly inactivated enzymes (see for example U.S. Pat. No. 5,773,258) can be employed in some embodiments of the present teachings.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930.

Photoligation using light of an appropriate wavelength as a ligation agent is also within the scope of the teachings. In some embodiments, photoligation comprises probes comprising nucleotide analogs, including but not limited to, 4-thiothymidine ($s^4T$), 5-vinyluracil and its derivatives, or combinations thereof. In some embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. In some embodiments, photoligation is reversible. Descriptions of photoligation can be found in, among other places, Fujimoto et al., Nucl. Acid Symp. Ser. 42:39-40 (1999); Fujimoto et al., Nucl. Acid Res. Suppl. 1:185-86 (2001); Fujimoto et al., Nucl. Acid Suppl., 2:155-56 (2002); Liu and Taylor, Nucl. Acid Res. 26:3300-04 (1998) and on the world wide web at: sbchem.kyoto-u.ac.jp/saito-lab.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, $3^{rd}$ Edition,; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 Febuary;4(1): 41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 Febuary;13(2): 294-307, and Landegren et al., Science 241:1077-80 (1988), Demidov, V., Expert Rev Mol Diagn. 2002 November;2(6):542-8., Cook et al., J Microbiol Methods. 2003 May;53(2): 165-74, Schweitzer et al., Curr Opin Biotechnol. 2001 Febuary;12(1):21-7, U.S. Pat. Nos. 5,830,711, 6,027,889, 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a linker probe that is annealed to a template in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linker probe, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol. 2004 Febuary;26(2):133-46. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584682 to Andersen et al.,). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

EXEMPLARY EMBODIMENTS

A common issue encountered in various approaches to detecting target polynucleotides is the molecular complexity of the reaction mixture. Such complex reaction mixtures can increase the likelihood of unwanted side reactions occurring, such as for example the formation of misligation products. Misligation products can subsequently be amplified and detected, thus resulting in a false positive. It is one aspect of the present teachings to reduce the unwanted propagation of such misligation products.

Figure 1:
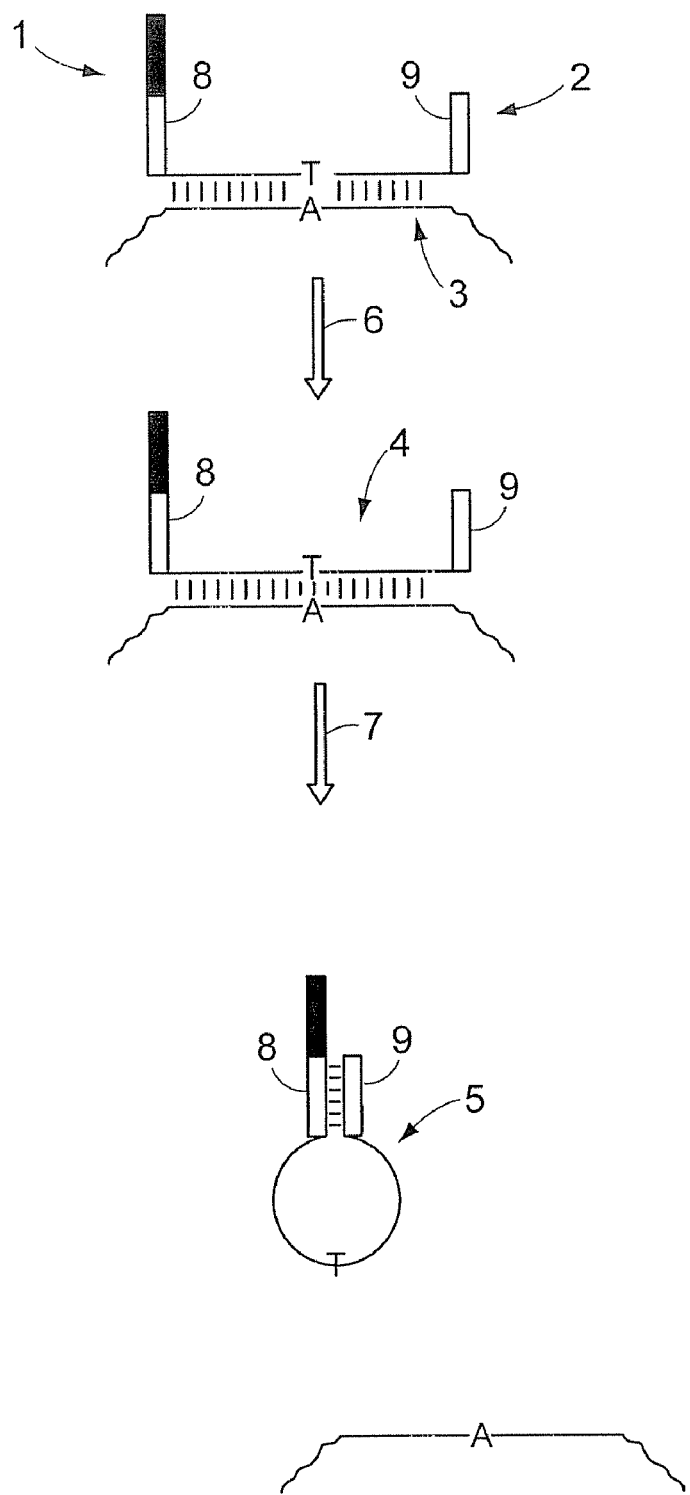
FIG. 1 illustrates a schematic embodiment contemplated by the present teachings.

FIG. 1 depicts the formation of a self-complementary ligation product. First, hybridization of a first probe (1) and a second probe (2) with a target polynucleotide (3) occurs. The first probe (1) comprises a single-stranded stem portion (8). The second probe (2) comprises a single-stranded stem portion (9). Ligation (6) of the first probe (1) with the second probe (2) results in the formation of a first ligation product (4). Dissociation (7) of the first ligation product from the target polynucleotide results in the formation of a self-complementary ligation product (5), wherein the single stranded stem portion of the first probe (8) hybridizes with the single stranded stem portion of the second probe (9).

Figure 2:
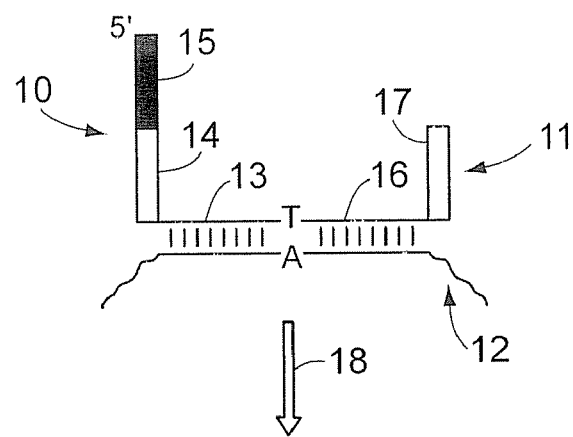
FIG. 2 illustrates a schematic embodiment contemplated by the present teachings.
Figure 2:
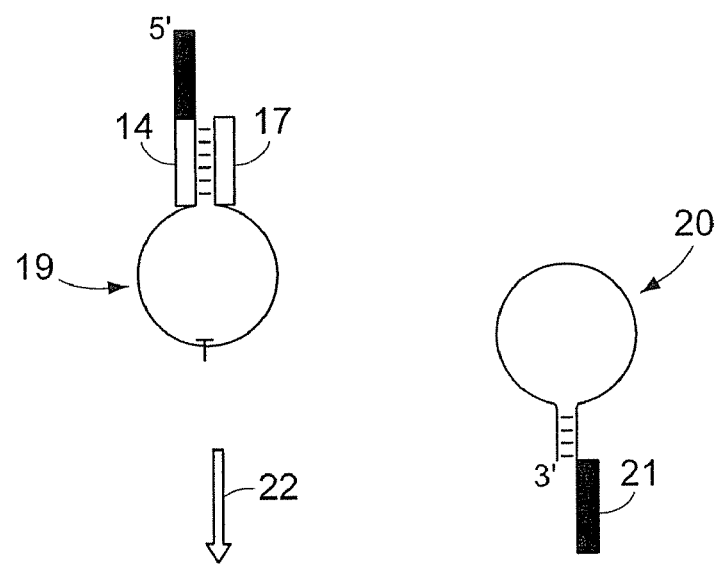
Figure 2:
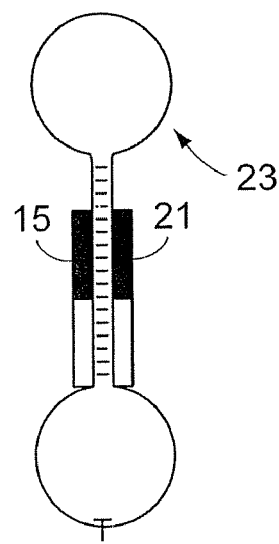

FIG. 2 depicts the formation of a loop ligation product according to some embodiments of the present teachings. Here, a first probe (10) and a second probe (11) are hybridized adjacently on a target polynucleotide (12). The first probe (10) comprises a target specific portion (13), a single stranded stem portion (14), and a protruding tail (15), wherein the terminal of the protruding tail is depicted as the 5' end of the molecule. The second probe (11) comprises a target specific portion (16) and a single stranded stem portion (17). Following ligation of the first probe (10) to the second probe (11) to form a first ligation product, and dissociation of the first ligation product (18), the single-stranded stem portion of the first probe (14) can hybridize to the single-stranded stem portion of the second probe (17) to form a self-complementary ligation product (19). Hybridization and ligation (22) of the self-complementary ligation product (19) with a hairpin linker (20) results in the protruding tail of the first probe (15) hybridizing to a protruding tail of the hairpin linker (21), and the formation of a loop ligation product (23), wherein the 5' end of the single stranded portion of the first probe is ligated to the 3' end of the hairpin linker, and the 5' end of the hairpin linker is ligated to the 3' end of the self-complementary ligation product. Detection of the loop ligation product can result in determination of the target polynucleotide.

FIG. 3 depicts one procedure according to some embodiments of the present teachings for determining the identity of a single nucleotide polymorphism. Here, a first probe one (24) comprising a discriminating region T is ligated to a second probe (26) on a target polynucleotide (27) comprising an A at the single nucleotide polymorphism. The first probe two (25) comprising a discriminating region G fails to hybridize and ligate, since the corresponding C allele is not present. Following ligation, the first ligation product can be dissociated from the target polynucleotide, and a self-complementary ligation product formed as a result of the hybridization of the single-stranded stem portion of the first probe one to the single-stranded stem portion of the second probe. A first hairpin linker (28) comprising a protruding tail complementary to the protruding tail of the first probe one (24) can hybridize to the self-complementary ligation product, and ligation can occur between the 5' end of the first probe one and the 3' end of the first hairpin linker and between the 3' end of the second probe and the 5'end of the hairpin linker to form a loop ligation product (30). A second hairpin linker (29) comprising a protruding tail (hatched) complementary to the protruding tail of the first probe two (hatched) fails to undergo ligation, since a corresponding first ligation product and self-complementary ligation product was not formed due to the absence of the C allele. Nucleases can degrade the unligated second hairpin linker (31) at its exposed 3'end, at its exposed 5' end, or at both its exposed 3' end and its exposed 5' end. The loop ligation product (30), on the other hand, is resistant to nuclease degradation due to its closed loop structure. The loop ligation product (30) can be amplified in an amplification reaction, here a PCR in which a first primer (32) and a second primer (33, shown here with a biotin affinity moiety, B) flank the loop portion of the loop ligation product. Following amplification (34), and isolation (35) of one strand of the amplification product (37) via the affinity moiety, a collection of mobility probes can be provided. The mobility probes can comprise a target-identifying portion complement that corresponds to a target identifying portion present in amplification product. Here, the shown mobility probe (36) corresponding to the amplified loop ligation product further comprises a mobility modifier (jagged) and a label (L). While not shown, it will be appreciated that a mobility probe corresponding to the other hairpin linker can be present yet does not hybridize to amplification product since the C allele is absent, the formation of a first ligation product, self-complementary ligation product, and loop ligation product did not occur, and, hence an amplification product comprising the loop of the second hairpin linker does not occur since the second hairpin linker (31) can be degraded during a nuclease treatment step. Elution (38) of the bound mobility probe can then be performed, and detection achieved by a mobility dependent analysis technique such as capillary electrophoresis. The distinct mobility conferred by the mobility modifier can be used to encode the identity of the A allele. Visualization can be achieved by the label L1.

Envisioning the schematic in FIG. 3 as but one reaction in a multiplexed reaction, one can assume a multiplexy level of N SNP loci, queried with N probe sets, assuming there are two possible allelic variants at each SNP locus. In such a hypothetical non-limiting scenario, the first probes for a given SNP locus have the same single stranded stem region, therefore there are N single stranded stem regions for the 2N first probes corresponding to the N probe sets for the N SNP loci. The first probes for a given SNP locus have different protruding tails, therefore, there are 2N protruding tails. These 2N protruding tails correspond with 2N hairpin linkers. Of course, each of the 2N hairpin linkers has a distinct protruding tail as well. Because the correspondence a given allele and a given protruding tail can vary according to the experimental design of the experimentalist, a finite set of 2N hairpin linkers can be used to query an infinite set of SNP loci with an infinite set of first probes and second probes.

To further illustrate, in some embodiments, 48 SNPs and their corresponding 96 or greater potential alleles can be queried using at least 96 first probes comprising 48 distinct first probe ones and 48 distinct first probe twos, 48 distinct second probes, and 96 distinct hairpin linkers. In such a scenario, the 96 hairpin linkers can be differ from one another in their protruding tails, and in their target-identifying portions. By flanking the target-identifying portion of each hairpin linker with a universal forward primer portion and a universal reverse primer portion, all 96 target-identifying portions can be amplified in a single PCR comprising a single primer pair.

As depicted in FIGS. 1-3, some embodiments of the present teachings provide for the formation of a self-complementary ligation product that can hybridize to and ligate with the corresponding protruding tail of a hairpin linker to form a loop ligation product. The circular nature of such a loop ligation product can result in a number of features. For example, in a first aspect misligated first and second probes do not form loop ligation products since their single stranded stem portions are not complementary, and a self-complementary structure capable of ligating to the appropriate hairpin linker will not form. As a result, misligated first and second probes will not be propagated in downstream reactions that require a self-complementary ligation product. In a second aspect, by providing primers corresponding to the loop of the hairpin linker, the loop ligation product is a PCR amplifiable structure, and the resulting amplicon has the characteristic that its sequence can chosen by the experimentalist, unlike the sequence of the target polynucleotide under inquiry. Since the sequence of the amplicon is under the control of the experimentalist, steps can be taken to minimize unwanted sequence characteristics and maximize desirable sequence characteristics so as to allow for robust and reproduce-able amplification. Such steps can facilitate the likelihood of success in highly multiplexed environments by minimizing unwanted cross-reactions between probes. In a third aspect, the loop ligation product can be resistant to certain nucleases, unlike the unincorporated probes, hairpin linkers, and target polynucleotides, which can be nuclease-sensitive. After treatment with nucleases that remove such unincorporated probes, hairpin linkers, and target polynucleotides, the nuclease-resistant loop ligation product can thus undergo downstream reactions such as amplification without the unwanted background of these unincorporated molecules. In a fourth aspect, without being held to any theory, energetic calculations indicate the preferential self-complementarity of a ligated product comprising a first probe and a second probe as compared to complementary base-pairing duplex formation between an unligated first probe and second probe. For a double stranded sequence comprising $$5'\text{GTCTGCAATCTG}3' \qquad \text{SEQ ID NO:1}$$

as compared with a hairpin linker comprising a double stranded sequence and a 70 nucleotide connecting single-stranded adenine loop $$5'\text{GTCTGCAATCTG}(A)_{70}\text{CACATTGCAGAC}3' \qquad \text{SEQ ID NO:2}$$

with simulation conditions of 55C, [5 nM] and [Salt] =0.385M. The calculated results for the double stranded sequenced are:

$\Delta G37C=-7.3$ kcal/mol, Tm=42C, and Fraction bound=0.74%

The results for the hairpin linker are:

$\Delta G37C=-1.9$ kcal/mol, Tm=61C, and Fraction bound=94.7%

Thus, these energetic calculations indicate the preferential self-complementarity of a ligated product comprising a first probe and a second probe as compared to complementary base-pairing duplex formation between an unligated first probe and second probe.

In some embodiments, probes can comprise characteristics that allow for their cleavage once they are incorporated into a loop ligation product. For example, uracil can be included in one or more molecules of the probe set. By incorporating uracil into a loop ligation product, treatment with various glycosylases, such as for example uracil-N-glycosylase (UNG) and uracil-D-glycoylase (UDG), can result in the breaking of the loop at those residues corresponding to uracil. The resulting single stranded product can then be manipulated in downstream reactions, such as for example in a PCR amplification. As another example, RNA can be included in one or more molecules in a probe set. By incorporating RNA into a loop ligation product, treatment with NaOH (base) can result in the breaking of the loop at those residues corresponding to the RNA. The resulting single stranded product can then be manipulated in downstream reactions, such as for example in a PCR amplification. As yet another example, sites recognized by restriction enzymes can be included in one or more molecules in a probe set. By incorporating a restriction enzyme site into a loop ligation product, treatment with the corresponding restriction enzyme can result in the breaking of the loop at those residues corresponding to the restriction enzyme site. The resulting single stranded product can then be manipulated in downstream reactions, such as for example in a PCR amplification.

Some Amplification Configurations of Ligation Products According to the Present Teachings Amplification of the loop ligation product can be performed in a variety of configurations, some embodiments of which are depicted in FIG. 4, where a loop ligation product formed in a manner analogous to FIG. 2 is shown. In some embodiments as depicted in FIG. 4A, PCR primers (39, 40) flanking a target-identifying portion located in the loop portion of the hairpin linker (41) can be employed, whereby a target-identifying portion, and not nucleic acid corresponding to the target polynucleotide, is amplified. By amplifying only hairpin linker sequence, efficiencies in amplification can be achieved, since the experimentalist can control the sequence of the hairpin linker, and minimize for example undesired-able sequence characteristics such as GC bias.

Figure 4A:
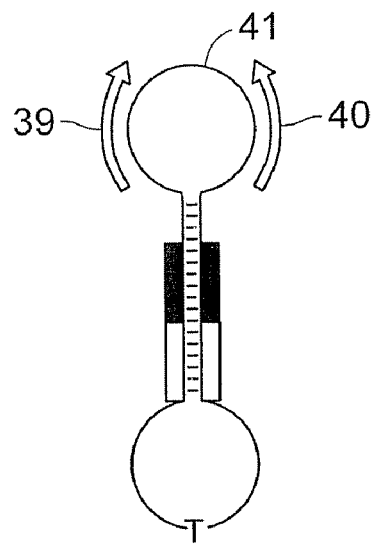
FIG. 4 illustrates some of the various components of a composition according to some embodiments of the present teachings.
Figure 4B:
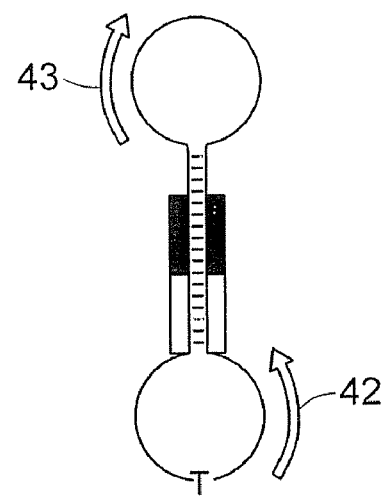

Another configuration for amplification is shown in FIG. 4B. Here, the second probe comprises a universal forward primer portion (42), and the loop of the hairpin linker comprises a universal reverse primer portion (43), wherein the orientation of the forward primer is pointed away from the SNP base. As a result, all the loop ligation products in a multiplexed reaction mixture can be amplified with the same universal reverse and universal forward primer pair, and all of the amplicons comprise sequence introduced by the experimentalist, with no sequence unique to the target polynucleotide. It will be appreciated that the location of the target identifying portion in such a configuration can be located between the flanking primers, such that the resulting amplicon comprises the target identifying portion. Further, the target-identifying portion can be located exclusively on the hairpin linker, can be shared between the hairpin linker and the self-complementary ligation product, or can be located exclusively on the self-complementary ligation product.

Figure 4C:
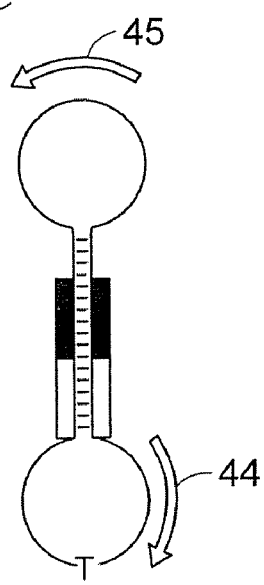

Another configuration for amplification is shown in FIG. 4C. Here, the second probe comprises a universal reverse primer portion (44), and the loop of the hairpin linker comprises a universal forward primer portion (45), wherein the orientation of the universal reverse primer is toward the SNP base. As a result, all the loop ligation products in a multiplexed reaction mixture can be amplified with the same universal reverse and universal forward primer pair, and since complete extension of the reverse primer to the hairpin linker requires a loop ligation product in order to form the substrate to which the forward primer hybridizes, background amplification should be minimal. Experiments using no template controls can illustrate a reduction in such background amplification. It will be appreciated that the location of the target identifying portion in such a configuration can be located between the flanking primers, such that the resulting amplicon comprises the target identifying portion. For example, the target-identifying portion can be located exclusively on the hairpin linker, can be shared between the hairpin linker and the self-complementary ligation product, or can be located exclusively on the self-complementary ligation product.

Figure 4D:
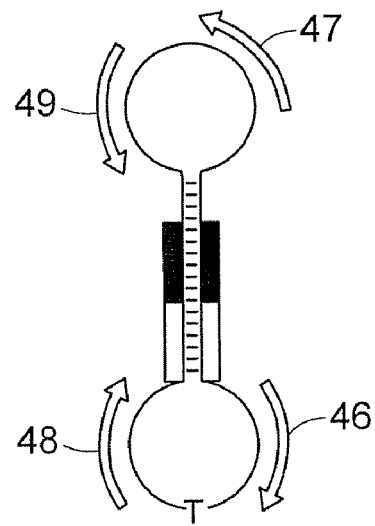

Another configuration for amplification is shown in FIG. 4D. Here, the second probe comprises a universal forward primer portion (47), and the loop of the hairpin linker comprises a universal reverse primer portion (46), wherein the orientation of the universal reverse primer is toward the SNP base. As a result, all the loop ligation products in a multiplexed reaction mixture can be amplified with the same universal reverse and universal forward primer pair, and since complete extension of the reverse primer to the hairpin linker requires a loop ligation product in order to form the substrate to which the forward primer hybridizes, background amplification should be minimal. Experiments using no template controls can illustrate a reduction in such background amplification. A secondary nested amplification can then be performed using the nested primers (48) and (49). This secondary nested amplification can be performed as a separate reaction, or in the alternative, the first primer pair (46, 47) can be of lower concentration and/or lower Tm relative to the second primer pair (48, 49), and both pairs of primers present in the same reaction, with alterations in reaction annealing temperatures conferring the two stages of amplification. It will be appreciated that the location of the target identifying portion in such a configuration can be located between the flanking primers (48, 49), such that the resulting nested amplicon comprises the target identifying portion. For example, the target-identifying portion can be located exclusively on the hairpin linker, can be shared between the hairpin linker and the self-complementary ligation product, or can be located exclusively on the self-complementary ligation product.

Figure 5:
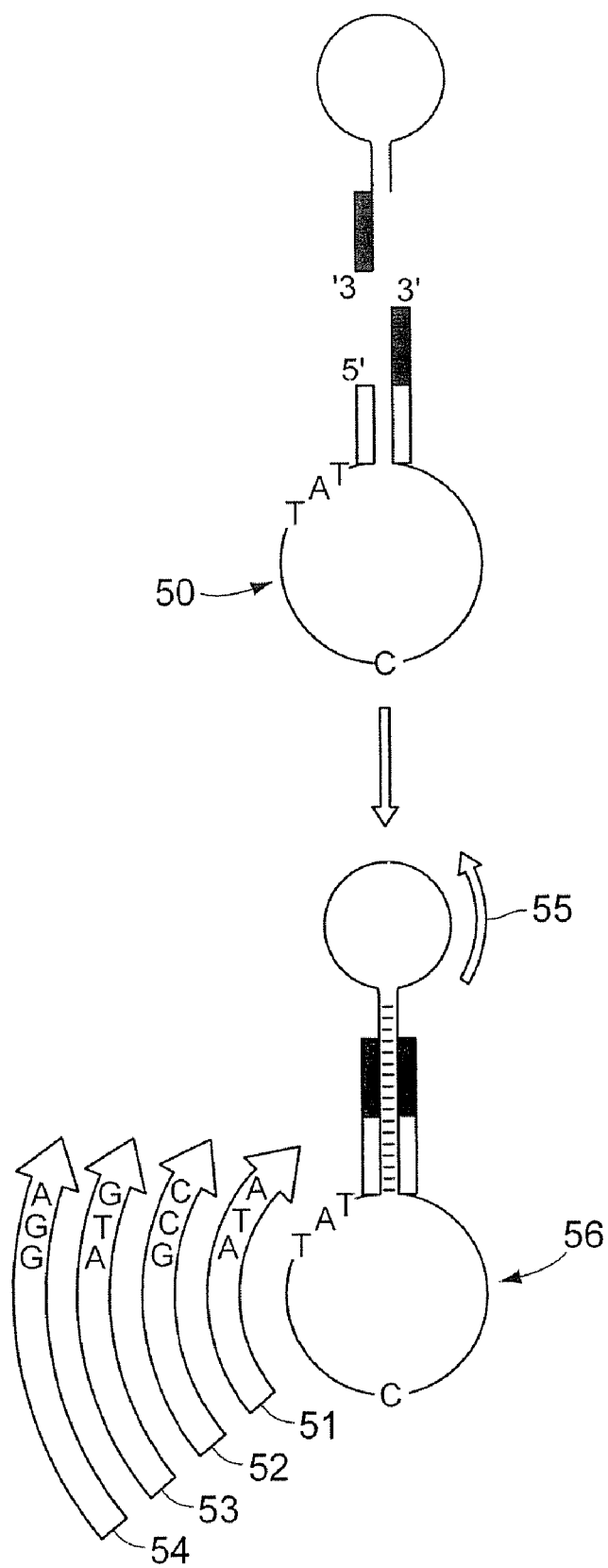
FIG. 5 illustrates a coding scheme according to some embodiments of the present teachings.

Another configuration for amplification is shown in FIG. 5. Here a context can be considered in which a hypothetical SNP locus with four allelic variants is queried. A first probe one, a first probe two, a first probe three, and a first probe four query the four different alleles. Each of the four first probes comprise a different universal reverse primer portion that differs not only in their discriminating regions, but also in the nucleotides located adjacent to the single stranded stem portion, shown in FIG. 5 top as an already formed self-complementary ligation product (50). Thus the identity of the allele is encoded in the nucleotides located adjacent to the single stranded stem portion which can co-vary along with the discriminating region. Four corresponding different universal reverse primers (51, 52, 53, and 54) can be used in the amplification reaction, such that only the appropriate first probe that forms a loop ligation product (56) is amplified with the corresponding universal reverse primer (here, 51, which has an ATA region that is complementary with the TAT of the loop ligation product). Another non-limiting aspect of the design depicted in FIG. 5, which can of course also be used elsewhere in the present teachings, is the presence of a single universal forward primer portion that resides on a single hairpin linker, thereby allowing a single universal forward primer (55) in the amplification along with the 4 different universal reverse primers. In such a scenario with N SNP loci each comprising 4 alleles, the N SNP loci can be queried with 4N first probes, N second probes, and only 1 hairpin linker. Of course, detection of the loop ligation products can comprise procedures such as incorporation of uracil etc to allow for the creating of a single stranded molecule for amplification. Further, detection of the amplification product can be achieved using any number of procedures, including a secondary ligation reaction, for example as discussed in U.S. Application US04/18396 to Lao, and shown for example in the context of FIG. 8.

Figure 6:
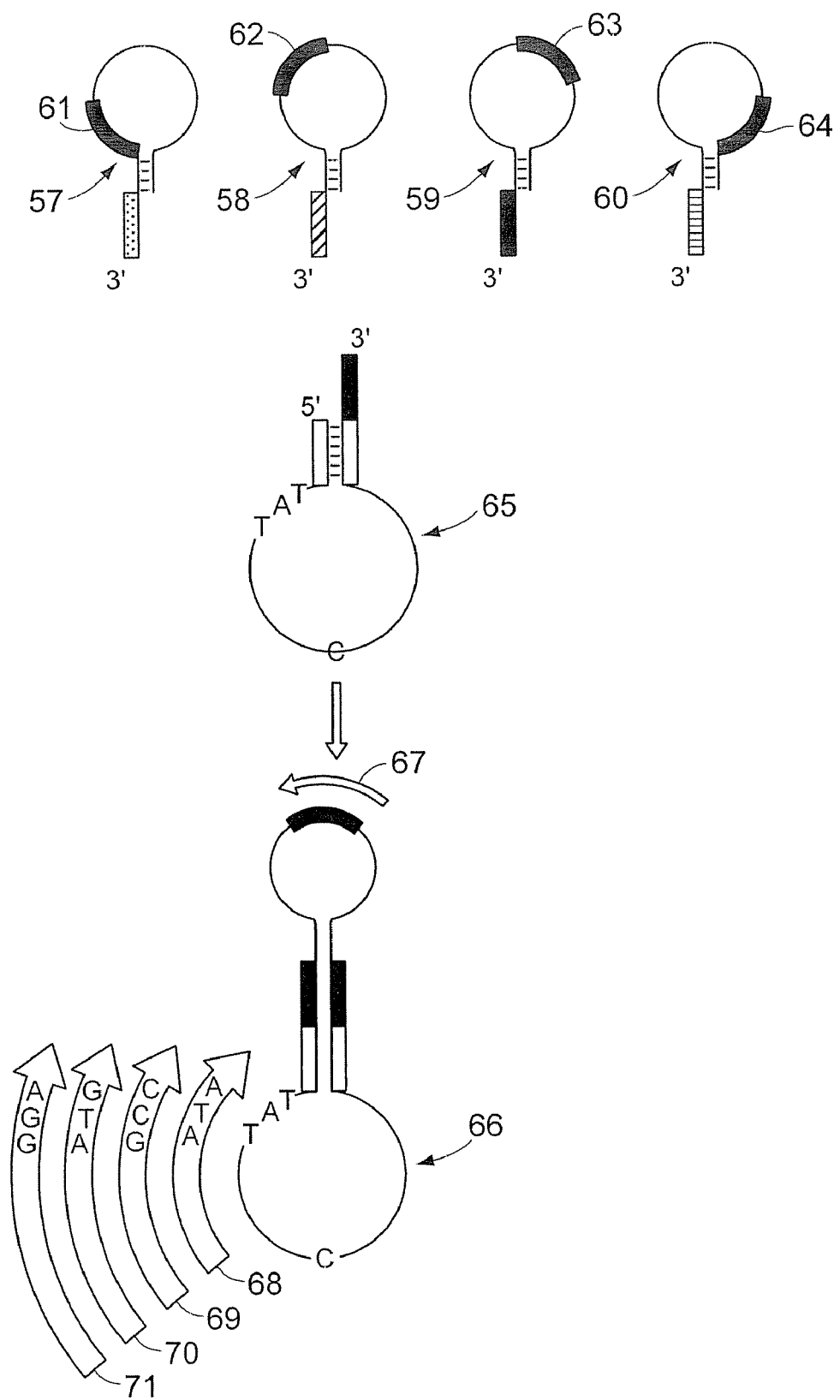
FIG. 6 illustrates a coding scheme according to some embodiments of the present teachings.

Another configuration for amplification is shown in FIG. 6. Here, a hypothetical SNP locus with four allelic variants is queried. A first probe one, a first probe two, a first probe three, and a first probe four query the four different alleles. Each of the four first probes comprise a different universal reverse primer portion that differs not only in their discriminating regions, but also differs in the nucleotides located adjacent to the single stranded stem portion. Thus the identity of the allele is encoded in the nucleotides located adjacent to the single stranded stem portion which can co-vary along with the discriminating region. Four different universal reverse primers can be used in the amplification, such that only the appropriate first probe that forms a loop ligation product is amplified with the corresponding universal reverse primer. A single universal forward primer portion can reside on a collection of hairpin linkers (57, 58, 59, and 60), wherein the location of the forward primer portion (61, 62, 63, 64) on the loop for a given hairpin linker can result in a size difference in the resulting amplicon. By labeling the four different universal reverse primers with a distinct label such as a florophore, and varying the position of the forward primer portion on the loop according to each hairpin linker/SNP locus, the amplification products can be detected directly with a mobility dependent analysis technique such as capillary electrophoresis. Here, hairpin linker (59) has a single stranded stem portion that is complementary to the single stranded stem portion of the self-complementary ligation product (65). As a result, the loop ligation product (66) can be amplified with a forward primer (67) at the corresponding forward primer portion of the hairpin linker 53, and the appropriate labeled reverse primer (68, bearing an ATA that is complementary with the TAT of the loop ligation product) thereby resulting in a labeled amplification product of a distinct size. (Of course, primers 69, 70, and 71, while in the PCR, do not hybridize and amplify target due to the absence of their respective encoded alleles in the target polynucleotide population, and the absence of corresponding loop ligation products.) In such a scenario, N SNPs can be queried with 4N first probes, N second probes, and N hairpin linkers. Of course, detection of the loop ligation products can comprise procedures such as incorporation of uracil etc to allow for the creating of a single stranded molecule for amplification. Further, detection of the amplification product can be achieved using any number of procedures, including a secondary ligation reaction, for example is discussed in U.S. Application US04/18396 to Lao, and shown for example in the context of FIG. 8.

Figure 7:
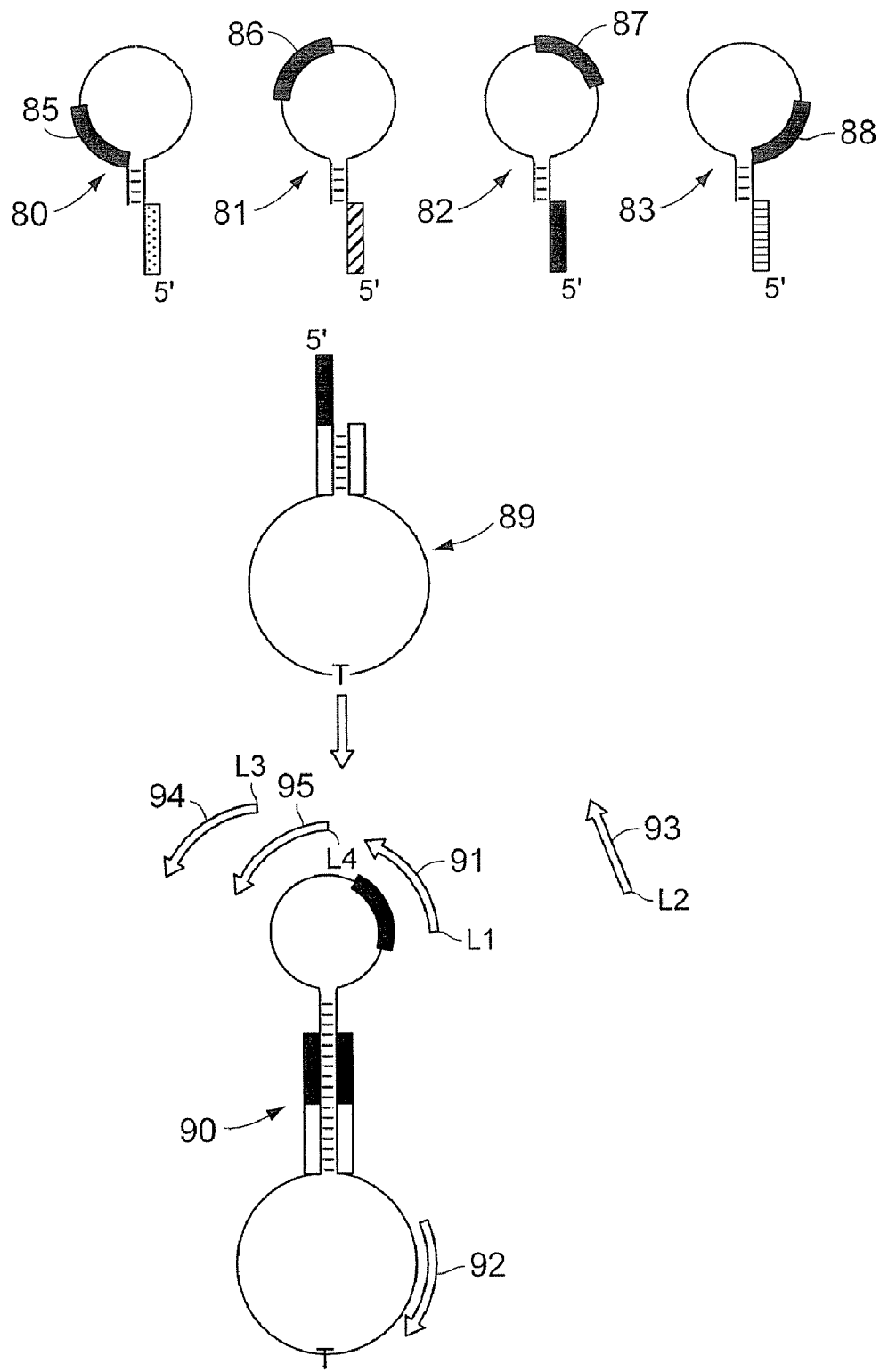
FIG. 7 illustrates a coding scheme according to some embodiments of the present teachings.

Another configuration for amplification is shown in FIG. 7. Here, four universal forward primer portions (85, 86, 87, and 88) can reside on a collection of four hairpin linkers (80, 81, 82, 83, and 84), wherein the location of the forward primer portion on the loop for a given hairpin linker can result in a size difference in the resulting amplicon. By using a four different universal forward primer sequences that are each labeled with a distinct label such as a florophore, four different universal forward primers can be provided that have different sequences and different labels. For example,

| | | |
|---|---|---|
| 5'AAGAAGAAGAAGAAGAAG3' | Red | SEQ ID NO:3 |
| 5'TTTTCCCCCCCCCTTTTTT3' | Blue | SEQ ID NO:4 |
| 5'CCAACCAACCAACCAACC3' | Green | SEQ ID NO:5 |
| 5'GGGGGGGGGGGGTTTTTT3' | Yellow | SEQ ID NO:6 |

By varying the position of the forward primer portion on the loop according to each hairpin linker/SNP locus, the amplification products can be detected directly with a mobility dependent analysis technique such as capillary electrophoresis. Here, hairpin linker (82) has a single stranded stem portion that is complementary to the single stranded stem portion of the self-complementary ligation product (89). Here, the second probe incorporated into the eventual loop ligation product (90) comprises a universal reverse primer portion to which a universal reverse primer (91) comprising a distinct label (L1) can hybridize, wherein the orientation of the universal reverse primer is toward the SNP base. As a result, all the loop ligation products in a multiplexed reaction mixture can be amplified with the same universal reverse primer (92) and one of the four different universal forward primers, and since complete extension of the reverse primer to the hairpin linker requires a loop ligation product, background amplification should be minimal. Experiments using no template controls can illustrate a reduction in such background amplification. The amplification products in this scenario will vary in their size due to the location of the forward primer portion on the loop. Further, the distinct label in each of the four universal forward primers can confer a distinct label to each amplification product. Here, the resulting amplicon will comprise a label L1, associated with universal forward primer (91). Universal forward primer (93) comprising label L2, universal forward primer (94) comprising label L3, and universal forward primer (95) comprising L4 are not detected, since their corresponding loop ligation product is not present.

As elsewhere in the present teachings, consideration of FIG. 7 will greet one of ordinary skill in the art with the appreciation that an additional level of mobility information and multiplexation can be achieved by taking advantage of length differences in the target polynucleotide, and the corresponding first and/or second probes.

Figure 8:
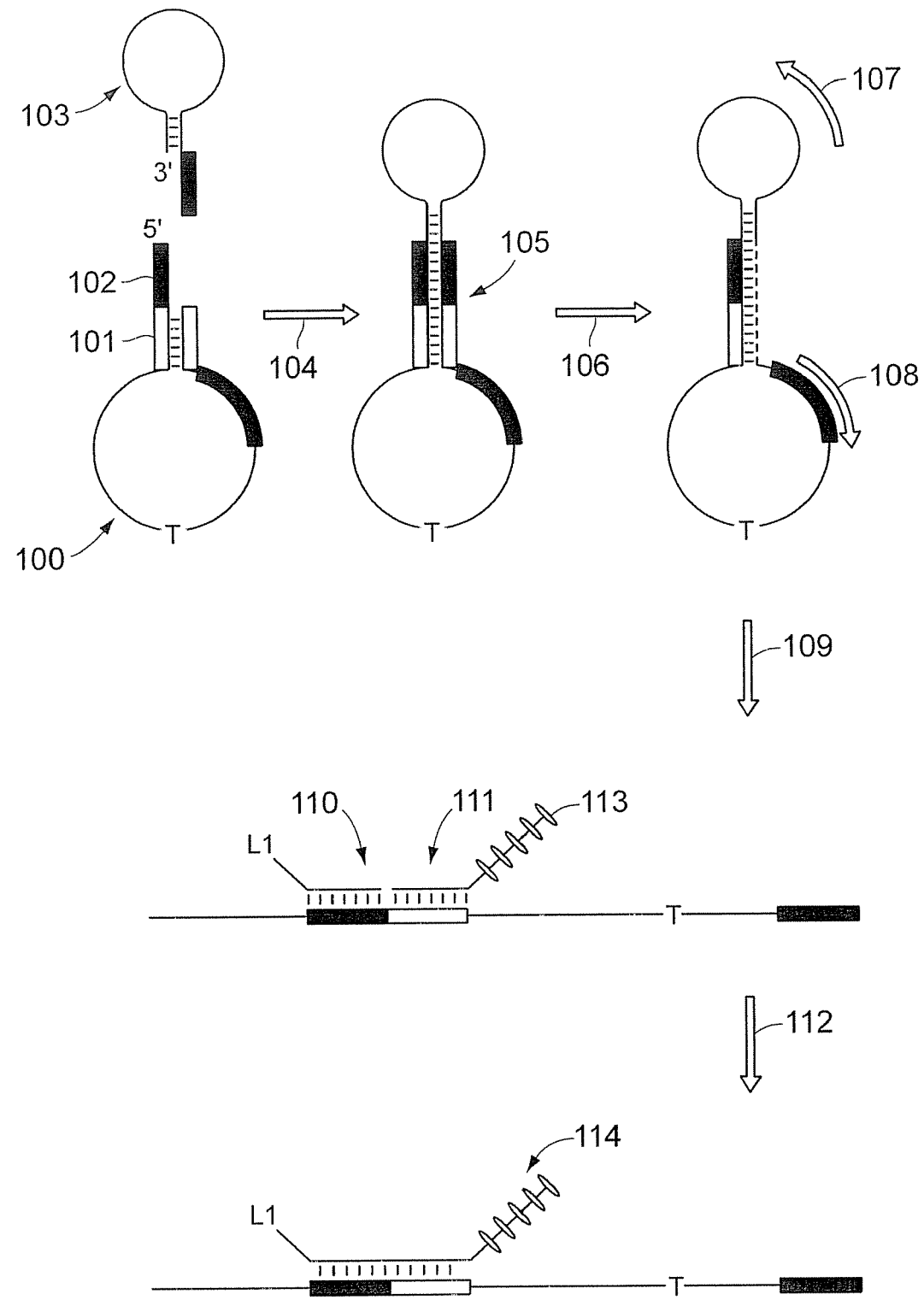
FIG. 8 illustrates a coding scheme according to some embodiments of the present teachings.

Another configuration for amplification is shown in FIG. 8. Here, a self-complementary ligation product (100) comprising a single stranded stem portion (101) and a protruding tail (102) is hybridized and ligated (103) with a corresponding hairpin linker (104) to form a loop ligation product (105) that can be amplified in a PCR (106) with a universal forward primer (107) and a universal reverse primer (108). Detection of the resulting amplicon can be achieved with an additional hybridization (109) of first detector ligation probe (110) to the region of the amplicon corresponding with the protruding tail of the self-complementary ligation product, hybridization (109) of a second detector ligation probe (111) to a region of the amplicon corresponding to the single stranded stem portion of the self-complementary ligation product, and the subsequent ligation (112) of the first detector ligation probe to the second detector ligation probe to form a detector ligation product. Here, the first detector ligation probe (110) further comprises a distinct label (L1) and the second detector ligation probe (111) comprises a distinct mobility modifier. The resulting detector ligation product (114) can be detected with a mobility dependent analysis technique such as capillary electrophoresis. The remaining unligated detector probes need not be washed and removed from the reaction mixture, since detection in a mobility dependent analysis technique can require both the presence of a distinct label and a distinct mobility, and as a result non-ligated detector probes will not be visualized. Additional teachings pertaining to a first ligation reactions followed by second detector ligation reaction can be found for example in Lao, U.S. Pat. Application US04/18396.

Partial Loop Ligation Products

Figure 9:
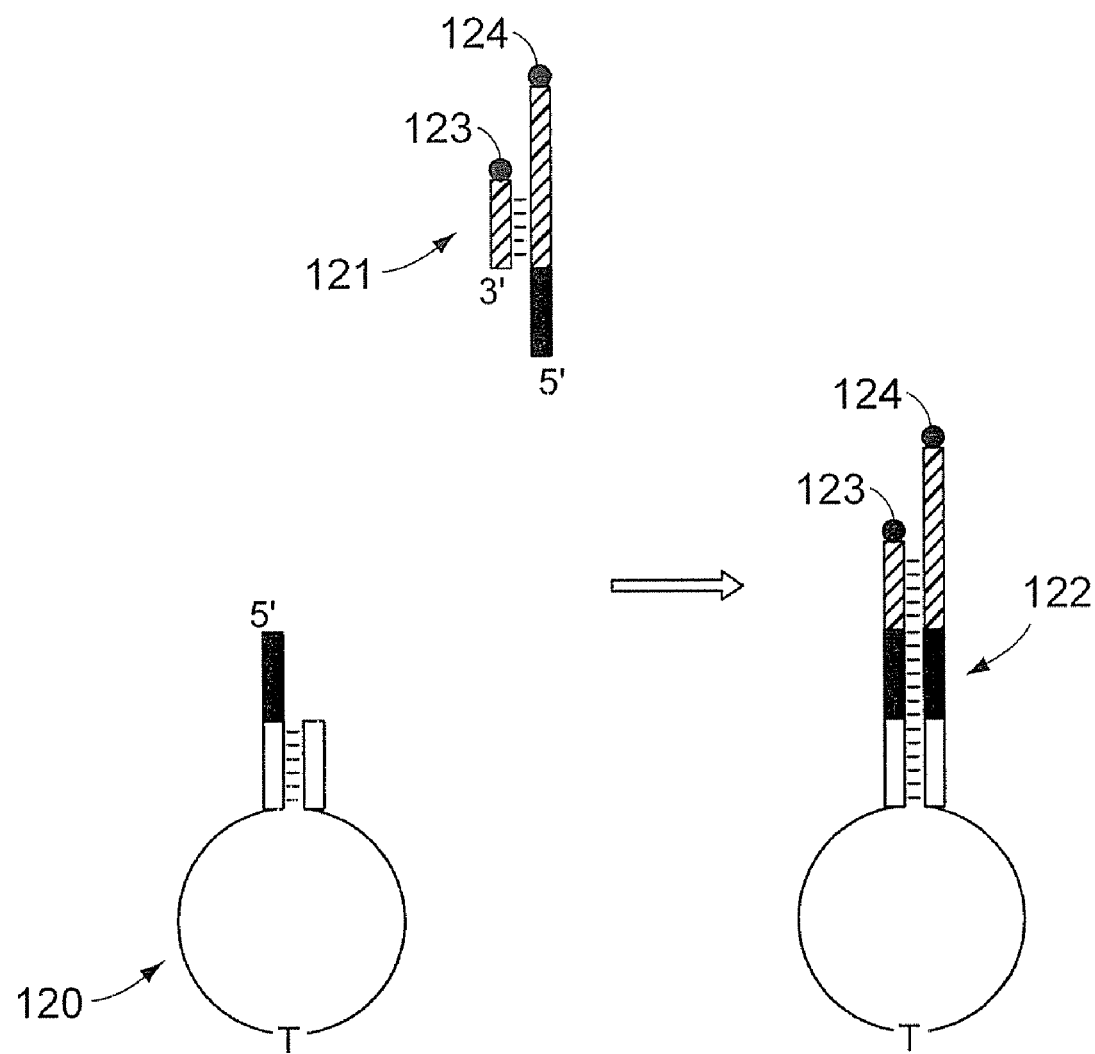
FIG. 9 illustrates a coding scheme according to some embodiments of the present teachings.

In some embodiments, the self-complementary ligation product is ligated to a non-hairpin linker that lacks a loop, and a partial loop ligation product is formed. For example, FIG. 9 depicts such a scenario wherein a self-complementary ligation product (120) is hybridized and ligated with a non-hairpin linker (121) to form a partial loop ligation product. Blocking moieties are depicted as (123) and (124). Moieties appropriate for the ends of such a blocking moiety can comprise any number of chemicals capable of, for example, conferring resistance to various nucleases, including PEG, C18, NH2, and tretramethoxyl uracil.

It will be appreciated that the foregoing figures comprising the formation of loop ligation products further conceive of scenarios in which an intermediary non-hairpin linker of the sort depicted in FIG. 9 is used to form a partial loop ligation product, albeit with the non-hairpin linker lacking blocking moieties. Hybridization and ligation of a hairpin linker to a partial loop ligation product made in such manner to then form a loop ligation product is clearly contemplated the present teachings.

Universal First Probe Library

Figure 10:
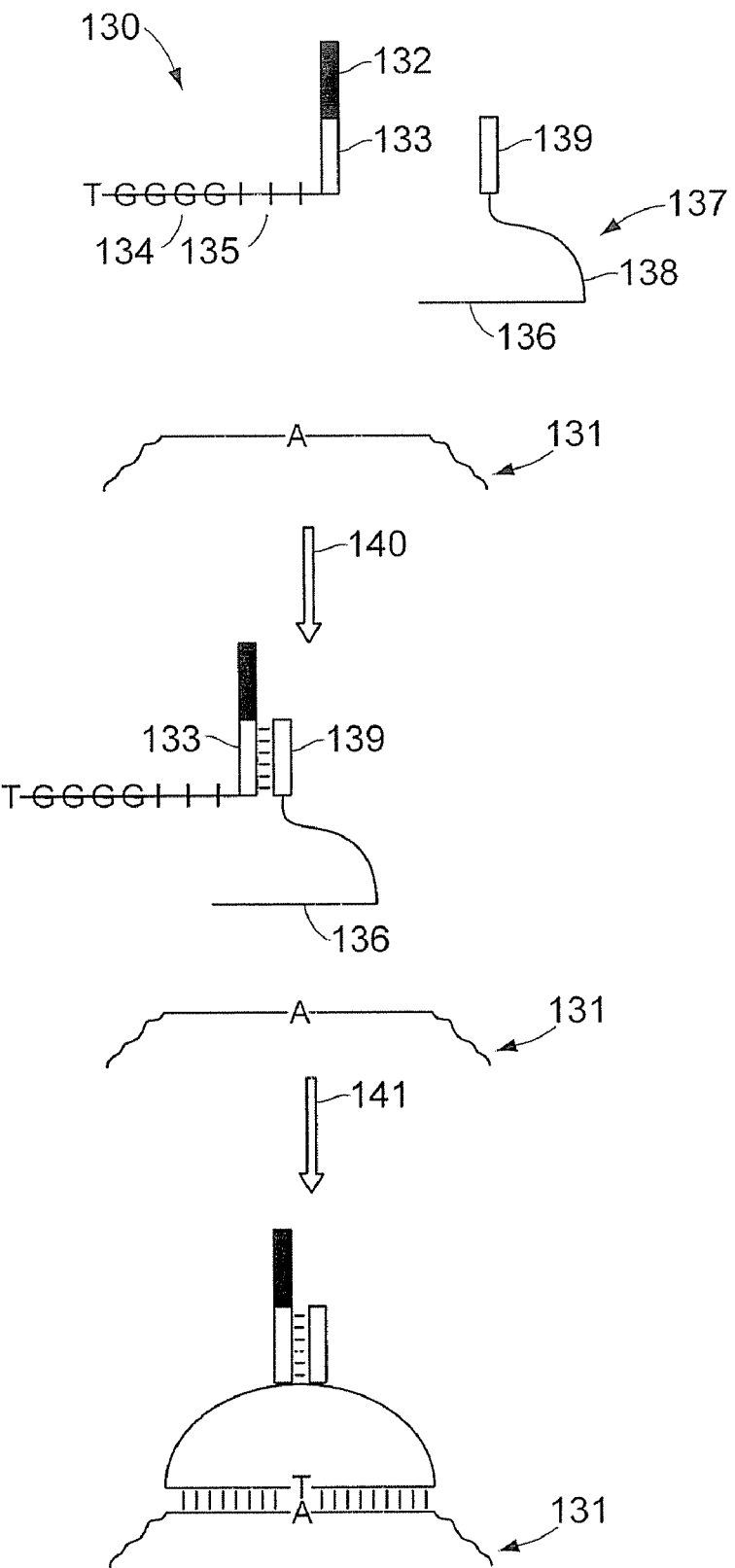
FIG. 10 illustrates a coding scheme according to some embodiments of the present teachings.

In some embodiments, a universal library of first probes can be employed. For example, a universal library of first probes can be applied to query an infinite number of SNP loci. In one embodiment of such a universal library of first probes, one can envision a collection of all possible 4-mers. Given the 4 nucleotides (A,T,G, and C) typically comprising a polynucleotide, there would thus be $4\uparrow 4$, or 256, such tetramers. Each of the four tetramers can be associated with a particular single-stranded stem portion, for a total of 256 different single-stranded stem portions. Further, placing one of the four nucleotides on the 3' end of each of the tetramers (to confer for example the functionality of a discriminating nucleotide) can result in a total of 256*4=1024 first probes. Each of the 1024 first probes can be associated with a particular protruding tail, for a total of 1024 protruding tails. A collection of 256 target polynucleotide specific second probes can comprise 256 different single stranded stem portions to correspond with the 256 different single stranded stem portions in the universal library of first probes. A representative interaction in such a scenario is depicted in FIG. 10. Here, one of the 1024 first probes (130) comprising one of 1024 protruding tails (132), one of 256 single stranded portions (133), one of 256 tetramers (GGGG, 134), universal bases for thermal stability (111, 135, representing for example inosine) and one of 4 discriminating nucleotides (T) is shown. Further, a target polynucleotide specific second probe is shown (137), comprising a target specific portion (136), a non-target specific portion (138) and a single-stranded stem portion (139). Following hybridization (140) of the single stranded stem portion of the first probe (133) with the single stranded portion of the second probe (139), hybridization (141) of the target specific portion of the second probe (136) to the target can occur, and hybridization (141) of the IIIGGGGT of the first probe to the target polynucleotide (103) can occur, resulting in a substrate suitable for ligation to form a self-complementary ligation product.

As elsewhere in the present teachings, analog bases such as LNA and/or PNA can be used in the probes to increase thermal stability. For example, the short 5-mers of the first probe that hybridize to the target in FIG. 10 can comprise LNA and/or PNA to confer increased thermal stability.

In some embodiments contemplated by the present teachings, the self-complementary ligation product can be hybridized with the hairpin linker to form a complex that is not ligated, that is, the hairpin linker is not ligated to the mature first ligation product. The resulting nicked circular structure can be detected, and/or amplified thereafter.

In some embodiments, the mature first ligation product can be hybridized with the hairpin linker to form a complex, wherein a gap of at least one nucleotide is present. In some embodiments, the gap can be filled in by a polymerase, and the resulting product ligated. In some embodiments, the gap can be filled in by a polymerase, and the resulting product not ligated. In some embodiments, the gap can be filled in by a polymerase, wherein the nucleotides used to fill in the gap are labeled, such that the resulting product is labeled.

Ligation

While the figures of the present teachings depict embodiments comprising a classical ligation reaction, it will be appreciated that a variety of ligation strategies are contemplated and within the scope of the present teachings. For example, gap-filling versions of ligation, as well as FEN-mediated version of ligation. Further, it will be appreciated that the ligation reactions can be cycled in ligase detection reaction (LDR) scenarios to achieve linear amplification of the first ligation products. In some embodiments, ligation can be performed using chemical ligation. In some embodiments, ligation can be performed using a chemical ligase. In some embodiments, ligation can be performed using a heat-stabile ligase. In some embodiments, ligation can be performed using a temperature-sensitive ligase (e.g. a 'hot-start' ligase). In some embodiments, the ligation can be performed in the context of a phosphorylation reaction, and/or decontamination reaction, as taught for example in Andersen et al., U.S. Provisonal Application 60/584682.

Amplification

The ligation products or ligation product surrogates can be amplified using any of a variety of amplification procedures. For example, PCR can be performed and the ligation products exponentially amplified. Alternativley, an asymmetric PCR can be performed and the ligation products linearly amplified. In other embodiments, rolling circle amplification can be performed. Generally, one of ordinary skill in the art will appreciate that a variety of amplification strategies can be performed to amplify the ligation products, and that applying such procedures would be routine and in no way require undue experimentation. For example, amplification according to the present teachings can encompass any manner by which at least a part of at least one target polynucleotide or hairpin linker is reproduced, typically in a template-dependent manner, including without limitation, a broad range of techniques for amplifying nucleic acid sequences, either linearly or exponentially. Exemplary steps for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions and combinations thereof. Descriptions of such techniques can be found in, among other places, Sambrook and Russell; Sambrook et al.; Ausbel et al.; PCR Primer: A Laboratory Manual, Diffenbach, Ed., Cold Spring Harbor Press (1995); The Electronic Protocol Book, Chang Bioscience (2002)("The Electronic Protocol Book"); Msuih et al., J. Clin. Micro. 34:501-07 (1996); The Nucleic Acid Protocols Handbook, R. Rapley, ed., Humana Press, Totowa, N.J. (2002)("Rapley"); Abramson et al., Curr Opin Biotechnol. 1993 Febuary;4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 Febuary;13(2):294-307, and Landegren et al., Science 241:1077-80 (1988), Demidov, V., Expert Rev Mol Diagn. 2002 November; 2(6):542-8., Cook et al., J Microbiol Methods. 2003 May;53(2):165-74, Schweitzer et al., Curr Opin Biotechnol. 2001 Febuary;12(1):21-7, U.S. Pat. Nos. 5,830,711, 6,027,889, 5,686,243, Published P.C.T. Application WO0056927A3, and Published P.C.T. Application WO9803673A1.

Amplification can comprise thermocycling or can be performed isothermally. In some embodiments, newly-formed nucleic acid duplexes are not initially denatured, but are used in their double-stranded form in one or more subsequent steps.

Primer extension is an amplifying step that comprises elongating at least one probe or at least one primer that is annealed to a template in the 5' to 3' direction using an amplifying means such as a polymerase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed probe or primer, to generate a complementary strand. In some embodiments, primer extension can be used to fill a gap between two probes of a probe set that are hybridized to target sequences of at least one target nucleic acid sequence so that the two probes can be ligated together. In some embodiments, the polymerase used for primer extension lacks or substantially lacks 5' exonuclease activity.

In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carrover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol, 2004 Febuary;26(2):133-46. In some embodiments, amplification can be achieved in a self-contained integrated approach comprising sample preparation and detection, as described for example in U.S. Pat. Nos. 6,153,425 and 6,649,378.

Detection

Detection and quantification can be carried out using a variety of procedures, including for example mobility dependent analysis techniques (for example capillary or gel electrophoresis), solid support comprising array capture oligonucleotides, various real time PCR approaches as well as end-point PCR analyses, various bead approaches (see for example Published P.C.T. Application WO US02/37499), including fiber optics, as well as flow cytometry (for example, FACS).

The use of capillary and gel electrophoresis for detection and quantification of target polynucleotides is well known, see for example, Grossman, et al., "High-density Multiplex Detection of Nucleic Acid Sequences: Oligonucleotide Ligation Assay and Sequence-coded Separation," Nucl. Acids Res. 22(21):4527-34 (1994), Slater et al., Current Opinion in Biotechnology, 2003, 14:1:58-64, product literature for the Applied Biosystems 3100, 3700, and 3730 capillary electrophoresis instruments, and product literature for the SNPlex Genotyping System Chemistry Guide, also from Applied Biosystems.

Additional mobility dependent analysis techniques that can provide for detection and quantification according to the present teachings include mass spectroscopy (optionally comprising a deconvolution step via chromatography), collision-induced dissociation (CID) fragmentation analysis, fast atomic bombardment and plasma desorption, and electrospray/ionspray (ES) and matrix-assisted laser desorption/ionization (MALDI) mass spectrometry. In some embodiments, MALDI mass spectrometry can be used with a time-of-flight (TOF) configuration (MALDI-TOF, see for example Published P.C.T. Application WO 97/33000), and MALDI-TOF-TOF (see for example Applied Biosystems 4700 Proteomics Discovery System product literature). Additional mass spectrometry approaches for detection and quantification are described for example in the Applied Biosystems Qtrap LC/MS/MS System product literature, the Applied Biosystems QSTAR XL Hybrid LC/MS/MS System product literature, the Applied Biosystems Q TRAP™ LC/MS/MS System product literature, and the Applied Biosystems Voyager-DE™ PRO Biospectrometry Workstation product literature.

In some embodiments of the present teachings, analysis of detected products can be undertaken with the application of various software procedures. For example, analysis of capillary electrophoresis products can employ various commercially available software packages from Applied Biosystems, for example GeneMapper version 3.5 and BioTrekker version 1.0.

In some embodiments, as illustrated schematically in FIG. 5, PCR amplified ligation products can be detected using mobility probes corresponding to target-identifying portions incorporated in the hairpin linkers, the mobility probes analyzed by a mobility dependent analysis technique such as capillary electrophoresis, where the distinct size of a mobility probe can encode the identity of a particular target polynucleotide. In addition to the distinct size of mobility probes, distinct labels can also be used to encode additional information and the identity of target polynucleotides.

In some embodiments, ligation products can be detected by various real-time PCR approaches such as TaqMan® (from Applied Biosystems. For example, the protruding tail of the hairpin linker can be used as a TaqMan probe binding site during a real-time cleaveage reaction. Alternatively, the single-stranded stem portion of the first probe and second probe can be used as a TaqMan probe binding site during a real-time cleaveage reaction. Alternatively, both the protruding tail of the hairpin linker and the single-stranded stem portion of the first probe and second probe can be used as a TaqMan probe binding site. It will be appreciated by one having ordinary skill in the art of molecular biology that variety of strategies can be performed to achieve selective hybridization of a TaqMan probe to a loop ligation product, and detection of the target polynucleotide determined accordingly. It will also be appreciated by one having ordinary skill in the art that the real time detection strategies employed to determine the target polynucleotide need not be limited to TaqMan probes, and that a variety of probes are known and routinely used for real-time detection of target polynucleotides. Further, it will be appreciated by one having ordinary skill in the art that end-point detection may be performed rather than real time approaches.

As another example of a detection scheme contemplated by the present teachings, the loop ligation product can comprise uracil and be treated with UNG to break the loop. The single stranded ligation product can then be amplified by a PCR. The resulting PCR amplicons can then serve as the substrate for a subsequent ligation reaction, wherein the ligation probes of this subsequent ligation can comprise a mobility modifier and a label, thereby allowing detection of the resulting ligation products on a mobility dependent analysis technique such as capillary electrophoresis. Exemplary teachings of a first ligation followed by a PCR, followed by a second ligation can be found for example in U.S. Application US04/18396 to Lao.

In some embodiments, detection can be achieved in a fashion comprising a multiplexed encoding ligation, wherein at least one probe querying a target polynucleotide includes a target-identifying portion. A plurality of different amplification reactions can be performed wherein the primers present in given amplification reaction can correspond with a given target identifying portion, thereby allowing for a single-plex amplification reaction to detect a particular target polynucleotide. Discussion of multiplexed encoding reactions followed by lower-plex and single plex amplification decoding reactions can be found for example in U.S. Non-Provisional applications Ser. Nos. 11/090,468, and 11/090,830.

Generally, the manner of performing detection is not a limitation of the present teachings.

Self-Complementary Primers in a PCR

The present teachings further contemplate embodiments comprising PCR, in which the PCR amplicon forms a self-complementary reaction product.

Figure 11:
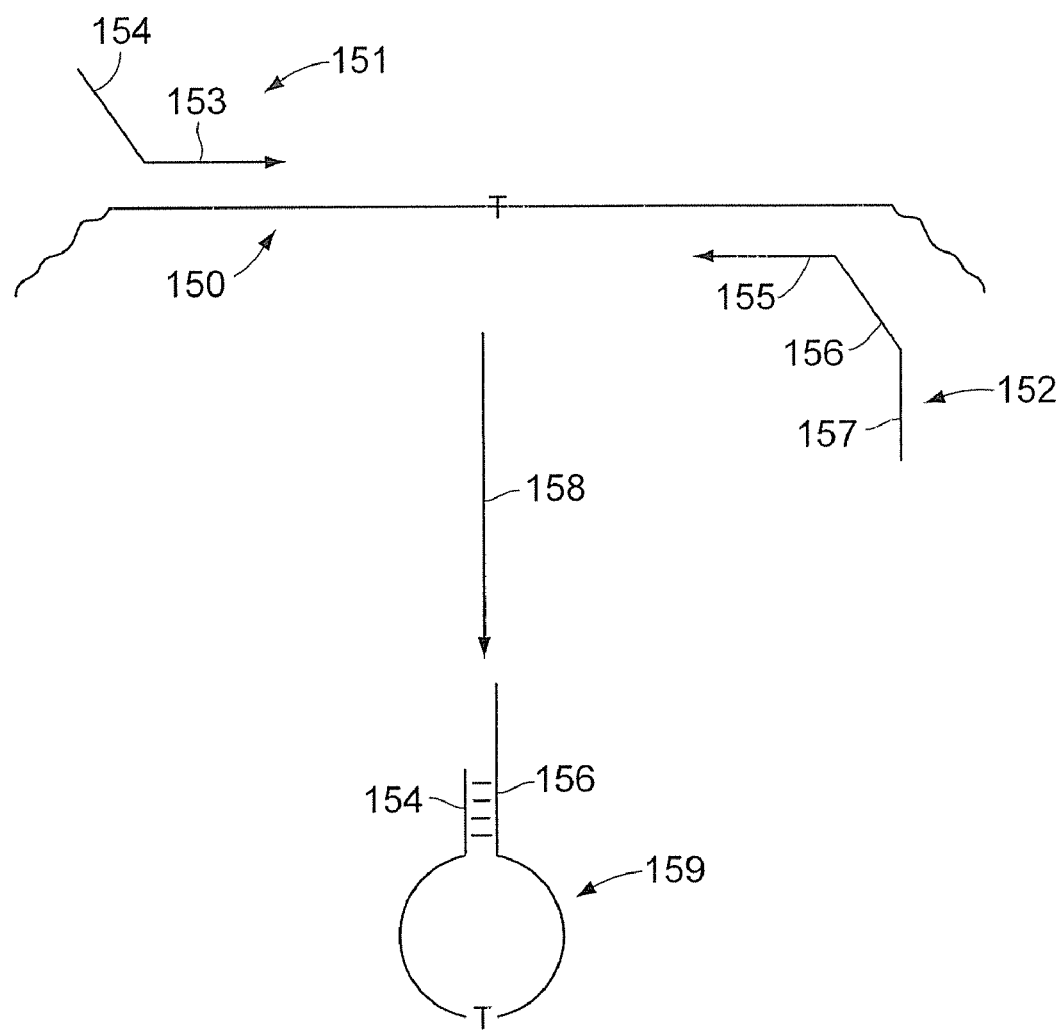
FIG. 11 illustrates a schematic embodiment contemplated by the present teachings.

For example, as shown in FIG. 11, a target polynucleotide (150) can be amplified with a forward primer (151) and a reverse primer (152). The forward primer can comprise a target specific portion (153) and a single-stranded stem potion (154). The reverse primer can comprise a target specific portion (155), a single-stranded stem portion (156), and a protruding tail (157). Following a PCR (158), a strand of the amplicon can for a self-complementary amplification product (159), with the single-stranded stem portions of the forward primer (154) and reverse primer (156) forming a double-stranded stem structure. It will be appreciated by one having ordinary skill in the art that the various illustrative linker probes, as well as encoding, amplification, and detection approaches discussed supra in the context of self-complementary ligation products can readily be applied in the context of self-complementary PCR products.

Some Additional Embodiments:

Some embodiments of the present teachings provide a step of amplifying, a step of ligating, a step of detecting, or combinations thereof.

Kits:

In some embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

Some embodiments of the present teachings provide a means for amplifying, a means for ligating, a means for detecting, or combinations thereof.

Some embodiments of the present teachings comprise a kit comprising a hairpin linker, a first probe, and a second probe, a ligase, a mobility probes, or combinations thereof, wherein the first probe comprises a single stranded stem portion that is complementary with a single stranded stem portion of the second probe, and wherein the hairpin linker comprises a protruding tail that is complementary with a protruding tail of the first probe.

Additional kit configurations are contemplated by the present teachings, as will be appreciated by one of ordinary skill in the art after reading the entirety of this application.

Aspects of the present teachings may be further understood in light of the following example, which should not be construed as limiting the scope of the teachings in any way.

EXAMPLE

Example 1 provides an illustration of the present teachings, wherein a multiplexed ligation reaction is performed with a ligation reaction mixture comprising a heat-activatable ligase, a uracil-N glycosylase, and a T4 polynucleotide kinase. This example comprises a 48-plex reaction, in which the identity of alleles as 48 bi-allelic SNP loci is determined.

The protocol is basically as follows: Genomic DNA is fragmented by boiling, quantified, and 37 ng/well is distributed and dried down into 384-well optical plates.

At room temperature, a master mix is pipetted, comprising:
20 mM Tris-HCl ph 7.6 at 25C
7 mM MgCl2
0.10% Triton X-100
1 mM DTT
1 mM NAD
5 units/ul heat-activatable ligase
0.1 units/ul T4 polynucleotide kinase
0.01 units/ul uracil-N-glycosylase (also, a control reaction without UNG can be performed)
0.05 mM Desferal
1.25 mM dATP
5% PEG 8000

At room temperature, 0.5 ul of probes and hairpin linkers are pipetted into each well of the 384-well optical plate using a Hydra II Plus One robot.

Master mix (4.5 ul per reaction) is pipetted into each well of the 384-well optical plate using a Hydra II Plus One robot.

A ligation reaction is performed on an Applied Biosystems GeneAmp PCR system 9700 with firmware 3.05 with the following cycling conditions:

| Step | Step Type | Temperature (C.) | Time |
| --- | --- | --- | --- |
| 1 | Hold | 37 | 60 minutes |
| 2 | Hold | 85 | 30 minutes |
| 2 | 30 cycles | 90 | 15 seconds |
|   |   | 60 | 30 seconds |
|   |   | 51 (with 2% ramp) | 30 seconds |
| 3 | Hold | 99 | 10 minutes |
| 4 | Hold | 4 | Hold indefinitely |

An exonuclease clean-up is then performed comprising:
For each reaction:
4.2 ul Nuclease-free water
0.5 ul Applied Biosystems SNPlex™ exonuclease buffer
0.2 ul Applied Biosystems SNPlex™ lambda exonuclease
0.1 ul Applied Biosystems SNPlex™ exonuclease 1
5 ul ligation reaction at 37C for 90 minutes, followed by 80 C for 10 minutes.

Following the exonuclease clean-up, 10 ul of water is added to each reaction, and a PCR amplification of the ligation products is performed. The PCR is performed in a Micro-Amp 384-well reaction plate (Applied Biosystems P/N 4309849) with an ABl Optical Adhesive Cover (P/N 4311971).

First, a 20X universal oligonucleotide primer mixture is formed comprising:
10 uM universal forward primer (UF 19)
10 uM biotinylated universal reverse primer (UR 19)
10 mM Tris HCl, pH 8.0 at 25C
1 mM EDTA

| Step | Step Type | Temperature (C.) | Time |
| --- | --- | --- | --- |
| 1 | Hold | 95 | 10 minutes |
| 2 | 30 cycles | 95 | 15 seconds |
|   |   | 70 | 60 seconds |
| 3 | Hold | 4 | Hold indefinitely |

Following the PCR, biotinylated strands are capture and separated, and mobility probes are hybridized to the immobilized strands. Eluted mobility probes are then detected via capillary electrophoresis on an Applied Biosystems 3730.

While the present teachings have been described in terms of these exemplary embodiments, the skilled artisan will readily understand that numerous variations and modifications of these exemplary embodiments are possible without undue experimentation. All such variations and modifications are within the scope of the current teachings.

What is claimed is:

1. A method of determining a target polynucleotide comprising;
providing a target polynucleotide, a primer set, and a hairpin linker,
wherein the primer set comprises a forward primer and a reverse primer,
wherein the reverse primer comprises a target specific portion, a single-stranded stem portion, and a protruding tail,
wherein the forward primer comprises a target specific portion, and a single-stranded stem portion,
wherein the hairpin linker comprises a loop portion, a stem portion, and a protruding tail,
wherein the single-stranded stem portion of the forward primer is complementary to the complement of the single-stranded stem portion of the reverse primer,
wherein the protruding tail of the hairpin linker is complementary to the protruding tail of the reverse primer;
amplifying the target polynucleotide in a polymerase chain reaction (PCR) using the forward primer and the reverse primer to form a first amplification product;
melting the first amplification product;
hybridizing the single-stranded stem portion of the forward primer to the complement of the single-stranded stem portion of the second primer to form a self-complementary amplification product;
hybridizing the protruding tail of the self-complementary amplification product to the protruding tail of the hairpin linker;
ligating the self-complementary amplification product to the hairpin linker to form a loop ligation product;
detecting the loop ligation product; and,
determining the target polynucleotide.

2. The method according to claim 1 wherein a plurality of target polynucleotides are determined, said method further comprising a plurality of target polynucleotides and a plurality of primer sets.

3. The method according to claim 1 further comprising amplifying the loop ligation product.

4. The method according to claim 3 wherein said amplifying comprises a PCR.

5. The method according to claim 4 wherein the loop portion of the hairpin linker further comprises a target-identifying portion, said method further comprising;
hybridizing the target-identifying portion of the loop ligation product to a mobility probe; and,
detecting the mobility probe with a mobility dependent analysis technique.

6. The method according to claim 5 wherein the mobility dependent analysis technique comprises capillary electrophoresis.

7. The method according to claim 4 wherein the amplifying comprises rolling circle amplification.

8. A reaction mixture comprising;
a target polynucleotide, a hairpin linker, a forward primer, and a reverse primer, wherein the forward primer comprises a single stranded stem portion that is complementary to the complement of a single stranded stem portion on the reverse primer, and wherein the hairpin linker comprises a protruding tail that is complementary to a protruding tail on the reverse primer.

9. The reaction mixture according to claim 8 further comprising a polymerase.

10. The reaction mixture according to claim 9 wherein the polymerase is temperature-sensitive.

11. The reaction mixture according to claim 8 further comprising a uracil-N-glycosylase.

12. A kit comprising a hairpin linker, a forward primer, and a reverse primer, wherein the forward primer comprises a single stranded stem portion that is complementary with the complement of a single stranded stem portion of the reverse primer, and wherein the hairpin linker comprises a protruding tail that is complementary with a protruding tail of the reverse primer.

13. The kit according to claim 12 further comprising a polymerase.

14. The kit according to claim 12 further comprising a mobility probe.

15. A method of forming a self-complementary amplification product comprising;
providing a target polynucleotide and a primer set,
wherein the primer set comprises a forward primer and a reverse primer,
wherein the forward primer comprises a target specific portion and a single-stranded stem portion,
wherein the reverse primer comprises a target specific portion and a single-stranded stem portion,
wherein the single-stranded stem portion of the forward primer is complementary with the complement of the single-stranded stem portion of the reverse primer;
amplifying the target polynucleotide in a polymerase chain reaction (PCR) with the forward primer and the reverse primer to form a first amplification product;
melting the first amplification product;
hybridizing the single-stranded stem portion of the forward primer to the complement of the single-stranded stem portion of the reverse primer; and,
forming a self-complementary amplification product.

16. A method of determining a target polynucleotide comprising;
providing a target polynucleotide, a primer set, and a hairpin linker,
wherein the primer set comprises a forward primer and a reverse primer,
wherein the reverse primer comprises a target specific portion, a single-stranded stem portion, and a protruding tail,
wherein the forward primer comprises a target specific portion, and a single-stranded stem portion,
wherein the hairpin linker comprises a loop portion, a stem portion, and a protruding tail,
wherein the single-stranded stem portion of the forward primer is complementary to the complement of the single-stranded stem portion of the reverse primer,
wherein the protruding tail of the hairpin linker is complementary to the protruding tail of the reverse primer;
amplifying the target polynucleotide in a polymerase chain reaction (PCR) with the forward primer and the reverse primer to form a first amplification product;
melting the first amplification product;
hybridizing the single-stranded stem portion of the forward primer to the complement of the single-stranded stem portion of the second primer to form a self-complementary reaction product;
hybridizing the protruding tail of the self-complementary reaction product to the protruding tail of the hairpin linker;
ligating the self-complementary reaction product to the hairpin linker to form a loop ligation product;
detecting the loop ligation product; and, determining the target polynucleotide.

* * * * *

SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Synthetic DNA

<400> SEQUENCE: 1
gtctgcaatc tg                                                         12

<210> SEQ ID NO 2
<211> LENGTH: 94
<212> TYPE: DNA
<213> ORGANISM: Artificial Sequence
<220> FEATURE:
<223> OTHER INFORMATION: Synthetic DNA

<400> SEQUENCE: 2
gtctgcaatc tgaaaaaaaa aaaaaaaaaa aaaaaaaaaa aaaaaaaaaa aaaaaaaaaa     60
aaaaaaaaaa aaaaaaaaaa aacacattgc agac                                 94

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
aagaagaaga agaagaag                                                   18

<210> SEQ ID NO 4
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
ttttcccccc cccttttttt                                                 19

<210> SEQ ID NO 5
<211> LENGTH: 18
<212> TYPE: DNA
<213> ORGANISM: Artificial Sequence
<220> FEATURE:
<223> OTHER INFORMATION: Synthetic DNA

<400> SEQUENCE: 5
ccaaccaacc aaccaacc                                                   18

<210> SEQ ID NO 6
<211> LENGTH: 18
<212> TYPE: DNA
<213> ORGANISM: Artificial Sequence
<220> FEATURE:
<223> OTHER INFORMATION: Synthetic DNA

<400> SEQUENCE: 6
gggggggggg gttttttt                                                   18